US010234271B2

(12) United States Patent
Fu et al.

(10) Patent No.: US 10,234,271 B2
(45) Date of Patent: Mar. 19, 2019

(54) METHOD AND SYSTEM FOR SPECTROSCOPIC BEAM PROFILE METROLOGY INCLUDING A DETECTION OF COLLECTED LIGHT ACCORDING TO WAVELENGTH ALONG A THIRD DIMENSION OF A HYPERSPECTRAL DETECTOR

(71) Applicant: KLA-Tencor Corporation, Milpitas, CA (US)

(72) Inventors: Jiyou Fu, San Jose, CA (US); Noam Sapiens, Cupertino, CA (US); Kevin A. Peterlinz, San Ramon, CA (US); Stilian Ivanov Pandev, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/100,843

(22) Filed: Aug. 10, 2018

(65) Prior Publication Data

US 2018/0347961 A1    Dec. 6, 2018

Related U.S. Application Data

(63) Continuation of application No. 14/960,121, filed on Dec. 4, 2015, now Pat. No. 10,072,921.

(Continued)

(51) Int. Cl.
 *G01B 11/00* (2006.01)
 *G01B 11/24* (2006.01)
 (Continued)

(52) U.S. Cl.
 CPC ............ *G01B 11/002* (2013.01); *G01B 11/24* (2013.01); *G03F 7/00* (2013.01); *G01B 2210/56* (2013.01);
 (Continued)

(58) Field of Classification Search
 CPC .. G01B 11/002; G01B 11/24; G01B 2210/56; G01N 21/956; G03F 7/00
 (Continued)

(56) References Cited

U.S. PATENT DOCUMENTS 5,429,943 A    7/1995 Kim et al.
5,608,526 A    3/1997 Piwonka-Corle et al.
(Continued)

FOREIGN PATENT DOCUMENTS

CN        1916603 A    1/2007
CN      101603921 A   12/2009
(Continued)

OTHER PUBLICATIONS

International Search Report dated Feb. 29, 2016, for PCT Application No. PCT/US2015/064150 filed on Dec. 5, 2015 by KLA-Tencor Corporation, 3 pages.

*Primary Examiner* — Que T Le
(74) *Attorney, Agent, or Firm* — Spano Law Group; Joseph S. Spano

(57) ABSTRACT

A spectroscopic beam profile metrology system simultaneously detects measurement signals over a large wavelength range and a large range of angles of incidence (AOI). In one aspect, a multiple wavelength illumination beam is reshaped to a narrow line shaped beam of light before projection onto a specimen by a high numerical aperture objective. After interaction with the specimen, the collected light is passes through a wavelength dispersive element that projects the range of AOIs along one direction and wavelength components along another direction of a two-dimensional detector. Thus, the measurement signals detected at each pixel of the detector each represent a scatterometry signal for a particular AOI and a particular wavelength. In another aspect, a hyperspectral detector is employed to simultaneously detect (Continued)

measurement signals over a large wavelength range, range of AOIs, and range of azimuth angles.

20 Claims, 12 Drawing Sheets

Related U.S. Application Data

(60) Provisional application No. 62/088,290, filed on Dec. 5, 2014.

(51) Int. Cl.
  *G03F 7/00* (2006.01)
  *G01N 21/21* (2006.01)
  *G01N 21/956* (2006.01)

(52) U.S. Cl.
  CPC ..... *G01N 21/956* (2013.01); *G01N 2021/213* (2013.01)

(58) Field of Classification Search
  USPC ..................................... 250/559.4, 221, 216
  See application file for complete search history.

(56) References Cited

U.S. PATENT DOCUMENTS

| | | |
|---|---|---|
| 5,859,424 A | 1/1999 | Norton et al. |
| 5,877,589 A | 3/1999 | Morgan et al. |
| 5,877,859 A | 3/1999 | Aspnes et al. |
| 6,580,509 B1 * | 6/2003 | Hutchin ............... G01J 3/2823 356/305 |
| 6,633,831 B2 | 10/2003 | Nikoonahad et al. |
| 6,734,967 B1 | 5/2004 | Piwonka-Corle et al. |
| 6,816,570 B2 | 10/2004 | Janik et al. |
| 6,895,075 B2 | 5/2005 | Yokhin et al. |
| 6,972,852 B2 | 12/2005 | Opsal et al. |
| 6,985,618 B2 | 1/2006 | Adel et al. |
| 7,248,375 B2 | 7/2007 | Opsal et al. |
| 7,352,453 B2 | 4/2008 | Mieher et al. |
| 7,463,369 B2 | 12/2008 | Wack et al. |
| 7,478,019 B2 | 1/2009 | Zangooie et al. |
| 7,502,101 B2 | 3/2009 | Raymond et al. |
| 7,515,279 B2 | 4/2009 | Raymond |
| 7,715,019 B2 | 5/2010 | Kiers et al. |
| 7,719,677 B2 | 5/2010 | Rosengaus |
| 7,734,437 B2 | 6/2010 | Tian et al. |
| 7,826,071 B2 | 11/2010 | Shchegrov et al. |
| 7,929,667 B1 | 4/2011 | Zhuang et al. |
| 7,933,026 B2 | 4/2011 | Opsal et al. |
| 3,030,631 A1 | 10/2011 | Norton et al. |
| 8,248,617 B2 | 8/2012 | De Groot et al. |
| 8,441,639 B2 | 5/2013 | Kandel et al. |
| 8,570,531 B2 | 10/2013 | Li |
| 8,699,027 B2 | 4/2014 | Wolf et al. |
| 2006/0033921 A1 | 2/2006 | Den Boef |
| 2009/0299655 A1 | 12/2009 | Biellak et al. |
| 2011/0043791 A1 | 2/2011 | Smilde et al. |
| 2011/0069312 A1 | 3/2011 | Kandel |
| 2011/0229830 A1 | 9/2011 | Bhattacharyya et al. |
| 2011/0246400 A1 | 10/2011 | Li |
| 2011/0310388 A1 | 12/2011 | Hill et al. |
| 2012/0120396 A1 | 5/2012 | Kandel et al. |
| 2012/0140511 A1 | 6/2012 | Artsyukhovich et al. |
| 2013/0042089 A1 | 2/2013 | Vihn et al. |
| 2013/0063721 A1 | 3/2013 | Fujii |
| 2013/0114085 A1 | 5/2013 | Wang et al. |
| 2013/0141730 A1 | 6/2013 | Quintanilha |
| 2013/0215404 A1 | 8/2013 | Den Boef |
| 2013/0229661 A1 | 9/2013 | Kandel et al. |
| 2013/0321810 A1 | 12/2013 | Wang et al. |
| 2014/0111791 A1 | 4/2014 | Manassen et al. |
| 2014/0139829 A1 | 5/2014 | Wolters et al. |
| 2014/0166862 A1 | 6/2014 | Flock |
| 2014/0172394 A1 | 6/2014 | Kuznetsov et al. |
| 2014/0222380 A1 | 8/2014 | Kuznetsov et al. |
| 2014/0297211 A1 | 10/2014 | Pandev et al. |
| 2014/0316730 A1 | 10/2014 | Shchegrov et al. |
| 2014/0375981 A1 | 12/2014 | Wang et al. |
| 2015/0042984 A1 | 2/2015 | Pandev et al. |
| 2015/0046118 A1 | 2/2015 | Pandev et al. |
| 2015/0204664 A1 | 7/2015 | Bringoltz et al. |
| 2016/0109375 A1 | 4/2016 | Pandev et al. |
| 2016/0161245 A1 | 6/2016 | Fu et al. |
| 2016/0169667 A1 | 6/2016 | Stork |

FOREIGN PATENT DOCUMENTS

| | | |
|---|---|---|
| CN | 103954589 A | 7/2014 |
| EP | 1309875 A2 | 5/2003 |
| WO | 2014016056 A1 | 1/2014 |
| WO | 2014074873 A1 | 5/2014 |
| WO | 2014082938 A1 | 6/2014 |
| WO | 2014138741 A1 | 9/2014 |

\* cited by examiner

METHOD AND SYSTEM FOR SPECTROSCOPIC BEAM PROFILE METROLOGY INCLUDING A DETECTION OF COLLECTED LIGHT ACCORDING TO WAVELENGTH ALONG A THIRD DIMENSION OF A HYPERSPECTRAL DETECTOR

CROSS REFERENCE TO RELATED APPLICATION

The present application for patent is a continuation of, and claims priority under 35 U.S.C. § 120 from, U.S. patent application Ser. No. 14/960,121, entitled "Methods and Systems for Spectroscopic Beam Profile Metrology having a first two dimensional detector to detect collected light transmitted by a first wavelength dispersive element," filed Dec. 4, 2015, which, in turn claims priority under 35 U.S.C. § 119 from U.S. provisional patent application Ser. No. 62/088,290, entitled "Method and Apparatus of Measuring a Property of a Substrate," filed Dec. 5, 2014, the subject matter of each is incorporated herein by reference in its entirety.

TECHNICAL FIELD

The described embodiments relate to metrology systems and methods, and more particularly to methods and systems for improved measurement of parameters characterizing semiconductor manufacturing processes and structures generated by semiconductor manufacturing processes.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput measurement without the risk of sample destruction. A number of optical metrology based techniques including scatterometry and reflectometry implementations and associated analysis algorithms are commonly used to characterize critical dimensions, film thicknesses, composition and other parameters of nanoscale structures.

In one example, two-dimensional beam profile reflectometers (2D-BPR) systems are employed to perform measurements of semiconductor samples. However, existing 2D-BPR systems acquire measurement signals one wavelength at a time. This limits the throughput of such systems when multiple illumination wavelengths are needed to accurately characterize the sample.

In another example, spectroscopic ellipsometry (SE) systems perform simultaneous measurements across a broad spectrum of illumination wavelengths. However, existing SE systems acquire measurement signals at one angle of incidence (AOI) at a time. This limits the throughput of such system when multiple AOIs are required to accurately characterize the sample.

Metrology applications involving the measurement of structures generated by semiconductor fabrication processes present challenges due to increasingly small resolution requirements, multi-parameter correlation, increasingly complex geometric structures, and increasing use of opaque materials. Thus, methods and systems for improved measurements are desired.

SUMMARY

Methods and systems for simultaneous detection of collected light over a broad range of angles of incidence and a broad range of wavelengths are presented herein. Several embodiments of a spectroscopic beam profile metrology system are presented herein for illustration purposes. In these embodiments, measurement signals over a large wavelength range and a large range of angle of incidence are simultaneously detected and used to determine values of parameters of interest. This enables measurements of critical dimensions (CD), overlay, thin films (TF), lithography focus, lithography dosage, roughness, and stress measurements with very short acquisition times using commercially available broadband light sources.

In one aspect, a spectroscopic beam profile metrology system includes a light source that emits a collimated beam of light with multiple wavelengths. Beam shaping optics reshape the collimated beam of light to a narrow line beam of light (e.g., sheet-like cross-section). The narrow line shaped beam of illumination light passes through a high numerical aperture (NA) objective that projects the narrow line beam of light onto the surface of the specimen under measurement over a broad range of angles of incidence. After interaction with the specimen, the spectroscopic beam profile metrology system includes a wavelength (i.e., energy) dispersive element that projects the collected beam of measurement light onto a two-dimensional detector. The wavelength components are dispersed across the detector in one dimension and the AOI components are projected across the detector in another direction. In this manner, the two-dimensional detector simultaneously detects both angular signal information (e.g., angle of incidence) and spectral information. Thus, the detected measurement signals at each pixel of the detector represent the scatterometry signal for a particular AOI and a particular wavelength.

In a further aspect, two or more wavelength dispersive elements and corresponding detectors are employed in the collection path to detect signals simultaneously or sequentially. Each wavelength dispersive element/detector pair is configured to detect different wavelength ranges. This may be advantageous for measurements over wide wavelength ranges, where a single detector and wavelength dispersive element is not able to measure across the entire wavelength range with sufficient accuracy.

In another further aspect, selectable illumination apertures and selectable collection apertures are configured to enable measurement of different targets. In some examples, light diffracted from the illuminated measurement site at a diffraction order different from a zero diffraction order is collected. In some other examples, light diffracted from the illuminated measurement site at the zeroth diffraction order is collected.

In another further aspect, a spatial light modulator (SLM) is located in the illumination path, the collection path, or both. The SLM is configured to modulate amplitude, phase distribution, or both, across the path of the illumination light, the collected light, or both, to reduce wavefront errors and shape the amplitude and phase distribution of the beam. In a further aspect, the spatial light modulator enables programmable configuration of the phase distribution across the illumination beam. This may be employed to correct aberrations or cancel contamination signals. In some embodiments, the SLM is a deformable mirror array.

In another further aspect, a polarizing element is located in the illumination path before the objective. In some embodiments, a stationary polarizer is employed. In these embodiments, two different polarization components may be detected by separate detectors. In some other embodiments, a continuously rotating polarizer is implemented. In these embodiments, an analyzer element is located in the collection path after the objective.

In another further aspect, a compensator is added in the illumination path after the polarizer and another compensator is added in the collection path before the analyzer.

In another further aspect, a beam shaping optic is located in the illumination path. The beam shaping optic is configured to rotate the narrow line beam illumination to a desired azimuth angle. By rotating the narrow line beam illumination about the beam axis, the effective azimuth angle is changed. For some two dimensional measurement targets, such as a CD line-space grating, and some three dimensional measurement targets, such as a complex fin structure, measurement sensitivity is improved when illumination is provided to the target at one or more specific azimuth angles.

In another further aspect, a spectroscopic BPR system is configured to scan the illumination beam along the AOI direction to enable a mapping of the pupil plane. In a further aspect, this pupil scanning mechanism may also be complemented with a second scanning mechanism that scans the field plane to enable averaging over target noise, a reduction of coherence effects, and improved accuracy.

In another further aspect, a spectroscopic BPR system includes beam shaping optics in the common path and the collection path. In this manner, the beam shape is a narrow line shape only before entering the objective and any wavelength dispersive elements.

In another further aspect, a spectroscopic BPR system includes two wavelength dispersive elements and two corresponding detectors. One detector is configured to perform pupil measurements of the specimen under measurement. The other detector is configured to perform field measurements of the same specimen.

In some embodiments, both field and pupil measurement signals are simultaneously detected. The detected signals are iteratively processed to estimate one or more structural or process parameter values. More specifically, the value of the at least one structural or process parameter associated with the at least one measurement target is determined based on an iterative regression of the pupil measurement signals with a pupil measurement model and regression of the field measurement signals with a field measurement model.

In some embodiments both field and pupil measurement signals are processed in a combined analysis to estimate one or more structural or process parameter values. In these examples, the measurement model is a combined measurement model that links structural parameters, material parameters, or a combination of structural and material parameters of the metrology target(s) for both pupil and field measurements.

In another further aspect, a spectroscopic BPR system includes a beam combining element in the measurement path before the objective. An auto-focus probe beam, a pattern recognition probe beam, or a combination of both, are combined with the illumination beam before entering the objective, and an auto-focus signal beam, a pattern recognition signal beam, or a combination of both, are extracted from the collection beam after exiting the objective.

In another aspect, a hyperspectral detector is employed to detect the spectral component of a spectroscopic beam profile metrology system.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
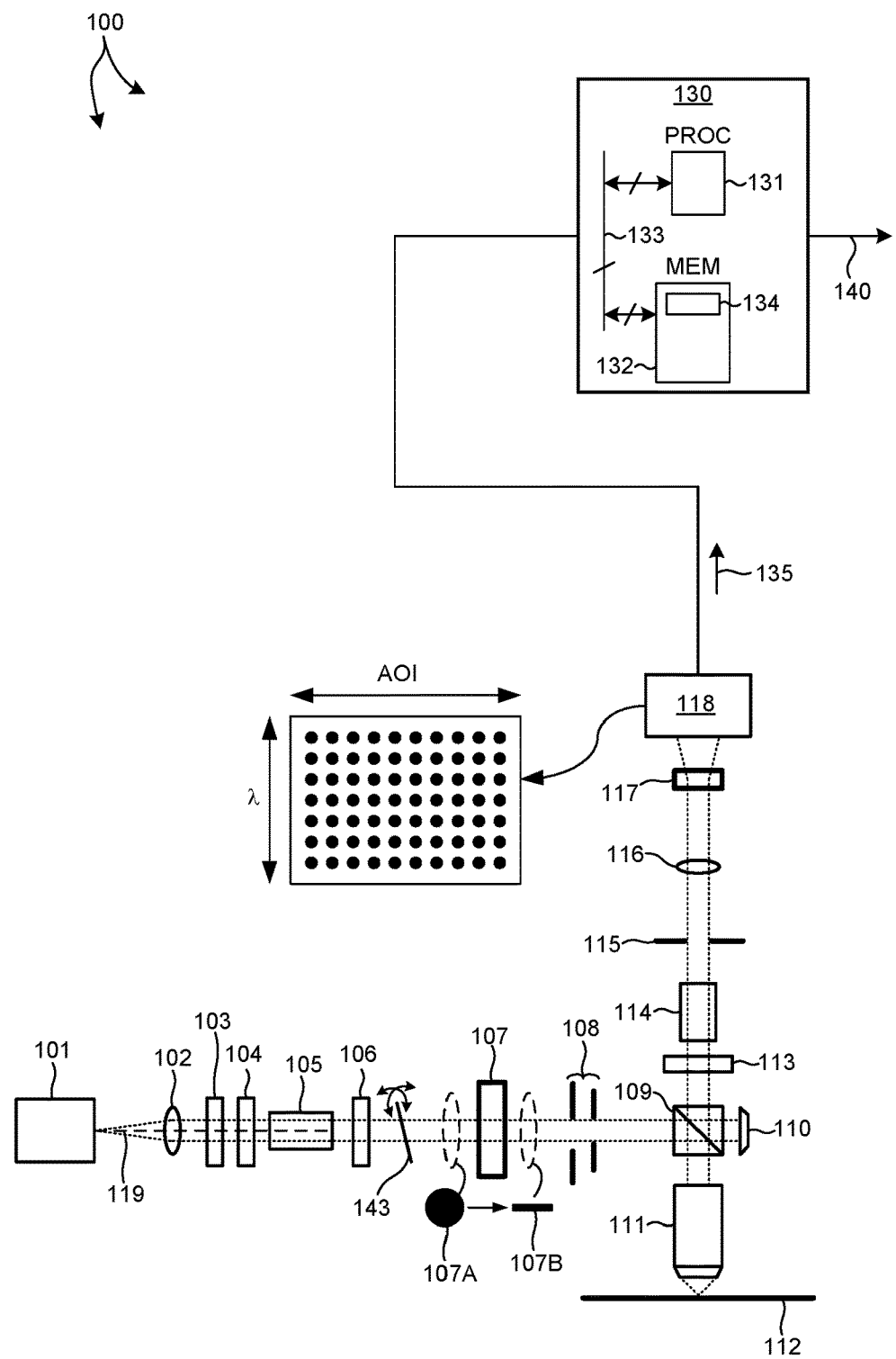
FIG. 1 illustrates an embodiment of a spectroscopic beam profile metrology system 100 for measuring characteristics of a specimen in accordance with the exemplary methods presented herein.

Reference will now be made in detail to background examples and some embodiments of the invention, examples of which are illustrated in the accompanying drawings.

Methods and systems for broadband illumination and simultaneous detection of collected light over a broad range of angles of incidence and a broad range of wavelengths are presented herein. Several embodiments of a spectroscopic beam profile metrology system are presented herein for illustration purposes. In these embodiments, measurement signals over a large wavelength range and a large range of angle of incidence are simultaneously detected and spectroscopic beam profile metrology signals generated by the detection subsystem are generated within a short integration time.

In one aspect, a spectroscopic beam profile metrology system includes a light source that emits a collimated beam of light with multiple wavelengths. Beam shaping optics reshape the collimated beam of light to a narrow line beam of light (e.g., sheet-like cross-section) that passes through a high numerical aperture (NA) objective that projects the narrow line beam of light onto the surface of the specimen under measurement over a broad range of angles of incidence. After interaction with the specimen, the spectroscopic BPR system includes a wavelength (i.e., energy) dispersive element that projects the collected beam of measurement light onto a two-dimensional detector. In this manner, the two-dimensional detector simultaneously detects both angular signal information (e.g., angle of incidence) and spectral information.

In one embodiment, one dimension of the detector is aligned along the line beam direction. In this dimension (i.e., the direction parallel to the line beam direction) the narrow line beam is dispersed on the detector as a function of angle of incidence (AOI). In addition, the wavelength dispersive element is oriented such that the direction of wavelength dispersion is perpendicular to the narrow line beam. Thus, in the second, orthogonal dimension of the two dimensional detector the narrow line beam is dispersed on the detector as a function of wavelength. Thus, the detected measurement signals at each pixel represent the scatterometry signal for a particular AOI and a particular wavelength. In some examples, the spectroscopic beam profile metrology system is a spectroscopic beam profile reflectometer (BPR) system. In these examples, the detected measurement signals at each pixel represent the reflectivity signal for a particular AOI and a particular wavelength.

In some of these examples, beam shaping optics reshape the beam from a circular shape to a line shape with negligible light loss. Thus, the spectroscopic BPR system has very high light efficiency. This enables measurements of critical dimensions (CD), overlay, thin films (TF), lithography focus, lithography dosage, roughness, and stress measurements with very short acquisition times using commercially available light sources, such as a xenon light, a laser driven plasma light source, a super continuum laser, etc.

FIG. 1 illustrates a system 100 for measuring characteristics of a specimen in accordance with the exemplary methods presented herein. As shown in FIG. 1, the system 100 may be used to perform pupil measurements of one or more structures of a specimen 112 that include both wavelength and AOI information dispersed across a two dimensional detector. In this aspect, the system 100 may be configured as a spectroscopic BPR. System 100 includes multiple wavelength illumination source 101, beam shaping optics 107, a high numerical aperture (NA) objective lens 111 (e.g., NA>0.7), a wavelength dispersive element 117, and a two dimensional detector 118. Detector 118 simultaneously acquires reflectivity signals over a range of AOI and a range of wavelengths from specimen 112. The reflectivity signals 135 are processed by computing system 130 to estimate one or more structural or process parameter values.

As depicted in FIG. 1, system 100 includes an illumination source 101 that generates an amount of illumination light 119 having multiple wavelengths. In some embodiments, illumination source 101 is a broadband illumination source such as an arc lamp (e.g., xenon lamp), a laser driven light source, a multiple wavelength laser, a supercontinuum laser, etc. In some other embodiments, illumination source 101 combines multiple narrowband light source such as multiple single wavelength lasers, tunable narrowband lasers, etc. In some embodiments, illumination source 101 includes a combination of broadband and narrowband illumination sources. In some embodiments, illumination source 101 includes multiple light sources emitting light across the deep ultraviolet, ultraviolet, visible, near infrared, and infrared spectra. Multiple light sources may be combined by one or more sliding mirrors, beam splitters, or any other suitable configuration. In general, illumination source 101 may include any combination of light sources. In one example, illumination source 101 includes one or more light sources spanning a range of wavelengths between 100 nanometers and 2,500 nanometers.

As depicted in FIG. 1, multiple wavelength illumination light 119 passes through collimation optics 102. Collimation optics 102 collimate the multiple wavelength illumination light 119. Collimation optics 102 include lens components, mirror components, or a combination of both. In one embodiment, the multiple wavelength illumination light 119 is collimated by an off-axis parabolic mirror (OAP) and becomes a collimated circular beam. In some examples, the collimation optics 102 are configured to adjust the illumination NA.

As depicted in FIG. 1, the multiple wavelength illumination light collimated by collimation optics 102 passes through one or more color filters 103. Color filters 103 select one or more illumination wavelength(s) and corresponding wavelength range(s) for measurement purposes, and absorb, or otherwise dissipate unwanted wavelengths. The one or more color filters 103 may include one or more optical filters, one or more color filter wheels, one or more linear varying edge filters, etc. The one or more color filters 103 may include one or more long pass filters, low pass filters, band-pass filters, etc. In general, it is advantageous to select one or more wavelength ranges appropriate to a given measurement application (e.g., CD, TF, Overlay, Focus, Dose, Roughness, stress, etc.).

Although, as depicted in FIG. 1, system 100 includes one or more color filters 103, in some other embodiments, color filters may not be employed. Thus, in general, the use of color filters is optional.

As depicted in FIG. 1, multiple wavelength illumination light 119 passes through beam shaping optics 107 located in the illumination path before objective 111. Beam shaping optics 107 are configured to reshape the incoming beam to a narrow line shape. In general, multiple wavelength illumination light 119 has a two dimensional intensity cross-section. As depicted in FIG. 1, the multiple wavelength illumination beam has a circular intensity cross-section 107A. After interaction with beam shaping optics 107, the multiple wavelength illumination beam has a narrow line intensity cross-section 107B that is approximately one dimensional (i.e., intensity cross-section substantially extends in one dimension, and does not substantially extend in an orthogonal dimension). Without beam shaping optics 107, the beam of illumination light 119 would be projected onto specimen 112 with spatially separated azimuth and AOI components. However, after reshaping by beam shaping optics 107, the azimuth components are collapsed in the direction across line 107B, effectively to a single azimuth value, while the AOI components are preserved in the direction along the line 107B. Although azimuth information is lost, this enables the detection of wavelength information as described hereinafter in further detail.

In one embodiment, a pair of cylindrical mirrors is employed to shape the incoming beam to a narrow line shape. In other embodiments, a cylindrical lens, a spatial light modulator (SLM), a diffractive optical element, a slit, or group of slits, or other suitable elements are employed to shape the beam to a narrow line shape.

In general, the incoming beam can be shaped into any approximately one-dimensional shape. Depending on particular measurement application factors such as target features, system aberrations (standard or field dependent), wafer shape, etc., other shapes may be contemplated such as dots, arcs, curved lines or any other suitable shape that enables collection of simultaneous angular and spectral information in accordance with the methods and systems described herein.

After reshaping by beam shaping optics 107, the narrow line illumination beam is directed to illumination beam splitter 109. Illumination beam splitter 109 may include any suitable beam splitting element including, but not limited to, a cubic beam splitter, a metallic coating plate, a dichroic optical coating plate, or other beam splitting mechanism. Illumination beam splitter 109 directs a portion of the collimated narrow line illumination to objective 111 and directs another portion to intensity monitor 110. In some embodiments, intensity monitor 110 is communicatively coupled to computing system 130 and provides an indication of the overall illumination intensity, the illumination intensity profile, or both, to computing system 130. Objective 111 directs collimated narrow line illumination to the surface of specimen 112 over a broad range of angles of incidence. Light reflected, diffracted, and scattered from the surface of specimen 112 is collected by objective 111.

In a preferred embodiment, objective 111 includes only reflective optical surfaces to accommodate the range of wavelengths potentially employed by the spectroscopic BPR systems described herein. In some examples, a reflaxicon objective is employed. Such an objective is capable of high NA (e.g., NA>0.9).

In some embodiments, the design of objective 111 may be optimized for substantially one-dimensional beams because, as described in FIG. 1, the intensity cross-section of the illumination beam entering objective 111 is substantially one-dimensional (e.g., narrow line shape).

In some embodiments, multiple objectives are located on a movable stage (e.g., motorized objective turret or motorized linear objective changer). In this manner, the selection of a particular objective may be programmably controlled, for example, by computing system 130. In this manner, different objectives may be made available to provide the best wavelength range and NA range for different measurement applications.

In general, high NA objective 111 may be catoptric (i.e., all reflective surfaces), catadioptric (i.e., combination of both reflective and refractive surfaces), or dioptric (i.e., all refractive surfaces).

Light collected by objective 111 is directed through a pupil detection path. The pupil detection path includes pupil relay optics 116 that direct the collected light to wavelength dispersive element 117. Wavelength dispersive element 117 disperses the collected light across one dimension of two dimensional detector 118 according to wavelength. Wavelength dispersive element 117 is oriented such that the direction of wavelength dispersion on the surface of the two dimensional detector 118 is perpendicular to the direction of dispersion of the collected light according to AOI.

A reflective grating is preferable for wide wavelength ranges. The grating density is selected to achieve the wavelength resolution for the measurement application. For example, if high wavelength resolution in the ultraviolet spectrum is required, a high density reflective grating or a prism is preferred. In general, wavelength dispersive element 117 may include at least one curved diffraction grating, planar diffraction grating, holographic plate, prism, or any other element suitable for spatially dispersing the collected light according to wavelength.

As depicted in FIG. 1, detector 118 is a two dimensional detector. In some embodiments, detector 118 is a two dimensional charge coupled device (2D-CCD). In some other embodiments, detector 118 is a two or three dimensional complementary metal oxide semiconductor (CMOS) sensor. In general, detector 118 may be any detector having separately addressable pixels, or other optically sensitive elements, arrayed in two dimensions. In this manner, both AOI and wavelength information can be separately resolved by system 100.

In a further aspect, two or more wavelength dispersive elements and corresponding detectors may be employed in the collection path to detect signals simultaneously or sequentially. Each wavelength dispersive element/detector pair is configured to detect different wavelength ranges. This may be advantageous for measurements over wide wavelength ranges, where a single detector and wavelength dispersive element is not able to measure across the entire wavelength range with sufficient accuracy. For example, one dispersion element and one detector is optimized for the ultraviolet to visible range, while another dispersion element and detector is optimized for the infrared range. Together, these detectors are capable of generating measurement signals over a broad spectral range. In one example, measurements across a wavelength range between 190 and 2,300 nanometers are desired. In this example, a wavelength dispersive element and a back-thinned CCD image sensor (e.g., back-thinned CCD image sensor model number S10420 manufactured by Hamamatsu Corporation (Japan)) is employed to perform measurements in the wavelength range between 190 and 1,000 nanometers. Another wavelength dispersive element and a photodiode array (e.g., InGaAs linear image sensor model number G9207-256W manufactured by Hamamatsu Corporation (Japan)) is employed to perform measurements in the wavelength range between 950 and 2,300 nanometers.

In some embodiments, a cascaded spectrometer design is employed to simultaneously detect measurement signals over different wavelength ranges. A sorting filter may be added to provide spectral separation between the higher order signal and the lower order signal. In one embodiment, wavelength range separation is achieved by a hot mirror or cold mirror. In another embodiment, wavelength range separation is achieved using a cascaded ultraviolet+infrared spectrometer design for wavelength separation and signal detection as described in U.S. Pat. No. 8,873,050 assigned to KLA-Tencor Corporation, the subject matter of which is incorporated herein by reference in its entirety.

In a further aspect, one or more illumination apertures are located in the illumination path before the beam shaping optics. In some embodiments, one or more apodizers or slits are located in the illumination path to reduce the measurement spot size. In some embodiments, the apodizers or slits are located in the illumination path to limit the range of measurement AOI.

As depicted in FIG. 1, the multiple wavelength illumination light 119 passes through one or more illumination apertures 104 located in the illumination path before beam shaping optics 107. The aperture(s) of the selectable illumination apertures 104 may be formed by any suitable device including, but not limited to a mechanical pin-hole, a spatial light modulator (SLM), an apodizer, and any other beam forming and controlling component or sub-system.

In some embodiments, an apodizer located in the illumination path is employed to reduce measurement spot size by attenuating the beam of illumination light before the beam is substantially reshaped by beam shaping optics 107. In some of these embodiments, apodizer 104 is selected to attenuate the light intensity profile to reduce edge diffraction effects.

Figure 12A:
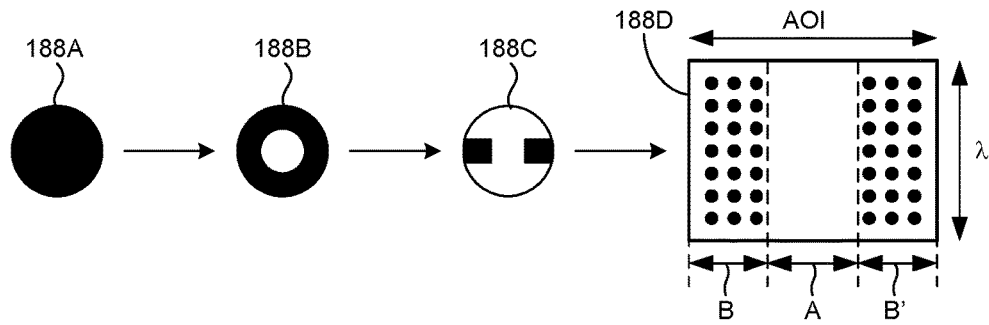
FIGS. 12A-12B illustrate beam intensity profiles associated with two different illumination apodizer and collection aperture selections that limit the AOI range to collect zeroth order diffracted light from a sample.

In some embodiments, apodizer 104 is selected to control the illumination NA range, and thus, the range of available AOI. In one example, depicted in FIG. 12A, specimen 107 under measurement includes a grating structure having a pitch of 500 nanometers. Illumination light 119 includes wavelength components in the range of 190-2,500 nanometers. In this example, apodizer 104 is selected to limit the range of illumination AOI within 32-65 degrees. This enables zeroth order diffraction signal collection in this example. FIG. 12A depicts the intensity cross-section 188A of collimated illumination beam 119 before interaction with apodizer 104. FIG. 12A also depicts the intensity cross-section 188B of collimated illumination beam 119 after interaction with apodizer 104. As depicted in FIG. 12A, apodizer 104 limits the range of illumination AOI by significantly attenuating the illumination intensity in the center of the beam (small AOI). FIG. 12A depicts the intensity cross-section 188C of the illumination beam as it enters objective 111. As illustrated in FIG. 12A, the intensity cross-section is influenced by the combination of apodizer 104 and the "flattening" of the intensity cross-section by beam shaping optics 107. FIG. 12A depicts the projection 189D of the collected light onto detector 118. In this example, a collection aperture 115 is employed to block collected light beams associated with an AOI less than 32 degrees. This effectively blocks collected light having a non-zero diffraction order. As a result, detector 118 senses light for AOIs within the range of 32-65 degrees (i.e., AOI regions, B and B', illustrated in FIG. 12A) and does not sense substantial light within the range of AOIs between 0 and 32 degrees (i.e., AOI region, A, illustrated in FIG. 12A).

Figure 12B:
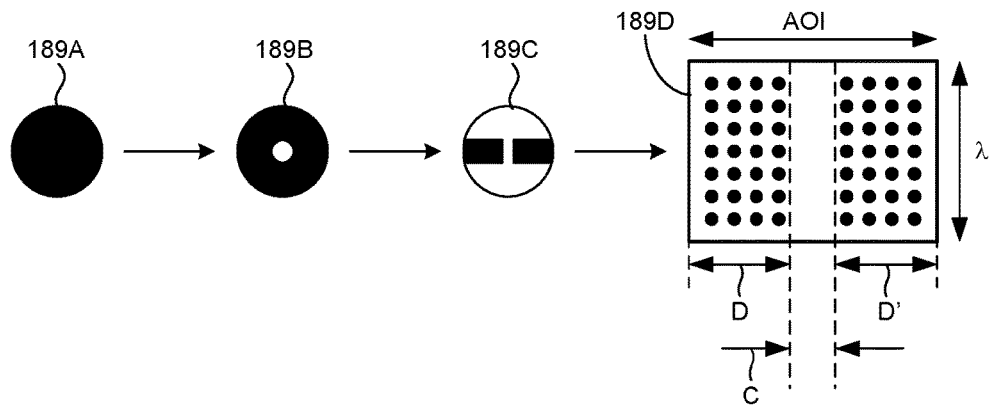

In another example, depicted in FIG. 12B, apodizer 104 is selected to limit the range of illumination AOI within 15-65 degrees. This also enables zeroth order diffraction signal collection in this example. FIG. 12B depicts the intensity cross-section 189A of collimated illumination beam 119 before interaction with apodizer 104. FIG. 12B also depicts the intensity cross-section 189B of collimated illumination beam 119 after interaction with apodizer 104. As depicted in FIG. 12B, apodizer 104 limits the range of illumination AOI by significantly attenuating the illumination intensity in the center of the beam (small AOI). FIG. 12B depicts the intensity cross-section 189C of the illumination beam as it enters objective 111. FIG. 12B depicts the projection 189D of the collected light onto detector 118. In this example, a collection aperture 115 is employed to block collected light beams associated with an AOI less than 15 degrees. This effectively blocks collected light having a non-zero diffraction order. As a result, detector 118 senses light for AOIs within the range of 15-65 degrees (i.e., AOI regions, D and D', illustrated in FIG. 12B) and does not sense substantial light within the range of AOIs between 0 and 15 degrees (i.e., AOI region, C, illustrated in FIG. 12B).

In some embodiments, illumination aperture 104 is a single aperture element. In some other embodiments, illumination aperture 104 is an array of aperture elements. In some examples, one or more aperture elements are located on a single degree of freedom motion stage or a multiple degree of freedom motion stage. In this manner, the presence or location of one of more aperture elements in the illumination path may be programmably controlled, for example, by computing system 130.

Although, as depicted in FIG. 1, system 100 includes one or more illumination apertures 104, in some other embodiments, illumination apertures may not be employed in the illumination path before beam shaping optics 107. Thus, in general, the use of illumination apertures is optional.

In a further aspect, one or more illumination apertures are located in the illumination path after the beam shaping optics. In some embodiments, the illumination apertures are located in the illumination path to reduce the measurement spot size. In some embodiments, the illumination apertures are located in the illumination path to limit the range of measurement AOI.

As depicted in FIG. 1, the multiple wavelength illumination light 119 passes through one or more illumination apertures 108 located in the illumination path after beam shaping optics 107. Illumination light passes through one or more selectable illumination apertures 108 before reaching illumination beam splitter 109. In some embodiments, the selectable illumination apertures 108 include a set of illumination field stops and a set of illumination pupil stops. The illumination field stops are configured to select the illumination spot size projected onto specimen 112. The illumination pupil stops are configured to select the illumination pupil projected onto specimen 112. The illumination field stops and pupil stops operate in conjunction with other illumination optics components (e.g., objective 106) to achieve an illumination NA tuned for optimal light throughput, illumination field of view, and pupil on the surface of specimen 112. The aperture(s) of the selectable illumination apertures 108 may be formed by any suitable device including, but not limited to a mechanical pin-hole, a spatial light modulator (SLM), an apodizer, and any other beam forming and controlling component or sub-system.

In some embodiments, illumination apertures 108 include a narrow slit or apodizer to control the size and intensity profile of the narrow line shaped beam. In one embodiment, illumination aperture 108 includes an apodizer to limit the range of AOIs as described with reference to FIGS. 12A-12B. In this manner, illumination apertures 108 may be used in conjunction with or as an alternative to apodizer 104.

Although, as depicted in FIG. 1, system 100 includes one or more illumination apertures 108, in some other embodiments, illumination apertures may not be employed in the illumination path after beam shaping optics 107. Thus, in general, the use of illumination apertures is optional.

In a further aspect, one or more collection apertures are located in the collection path after objective 111. In some embodiments, the collection apertures are located in the collection path to select a portion of the collected beam for detection by detector 118.

As depicted in FIG. 1, the collected light passes through one or more collection apertures 115 located in the collection path after objective 111. Collected light passes through one or more selectable collection apertures 115 before reaching wavelength dispersive element 117 and detector 118.

In the examples described with reference to FIGS. 12A-12B, an illumination apodizer and a collection aperture were selected to collect 0th order diffracted light from a sample by limiting the AOI range. For example, to acquire the zeroth order signal from a 500 nanometer pitch grating target, both the illumination apodizer and the collection aperture included a center blockage to limit the range of AOIs subject to detection. More specifically, the center blockage of the collection aperture effectively blocks the negative 1st order diffracted light from reaching detector 118.

In another embodiment, collection aperture 115 includes a narrow slit to further reduce the beam line width of the collected light before dispersion by wavelength dispersive element 117.

In some other examples, one or more illumination apertures and one or more collection apertures are selected to collect higher order diffracted light from a sample with a limited AOI range.

The aperture(s) of the selectable collection apertures 115 may be formed by any suitable device including, but not limited to a mechanical pin-hole, a spatial light modulator (SLM), an apodizer, and any other beam forming and controlling component or sub-system.

In some embodiments, collection aperture 115 is a single aperture element. In some other embodiments, collection aperture 115 is an array of aperture elements. In some examples, one or more aperture elements are located on a single degree of freedom motion stage or a multiple degree of freedom motion stage. In this manner, the presence or location of one or more aperture elements in the collection path may be programmably controlled, for example, by computing system 130.

Although, as depicted in FIG. 1, system 100 includes one or more collection apertures 115, in some other embodiments, collection apertures may not be employed. Thus, in general, the use of collection apertures is optional.

In another further aspect, a spatial light modulator (SLM) is located in the illumination path, the collection path, or both. In some embodiments, the SLM is located in an optical pupil plane of the measurement system. The SLM is configured to modulate amplitude, phase distribution, or both, across the path of the illumination light, the collected light, or both, to reduce wavefront errors and shape the amplitude and phase distribution of the beam. In a further aspect, the spatial light modulator enables programmable configuration of the phase distribution across the illumination beam. This may be employed to correct aberrations or cancel contamination signals. By way of non-limiting example, any of a transmissive liquid crystal display (LCD) device, a reflective liquid crystal on silicon (LCOS) device, a pixelated mirror device, and a deformable mirror device having a continuous surface may be employed as a SLM in the illumination path of a metrology system. A deformable mirror element includes a programmable surface shape. In particular optical aberrations that arise from objective 111, apodizer 104, cylindrical mirrors of beam shaping element 107, and other optical components may be compensated by one or more SLMs such as a deformable mirror array.

In another further aspect, a polarizing element is located in the illumination path before the objective. In some embodiments, the polarizing element is located before the beam shaping optics. In some other embodiments, the polarizing element is located between the beam shaping optics and the objective.

In yet another further aspect, an analyzer element is located in the collection path after the objective.

As depicted in FIG. 1, the multiple wavelength illumination light 119 passes through polarizer 105, and collected light passes through analyzer 114. In some embodiments, polarizer 105 is a static, or selectable, polarizing element. In some embodiments, polarizer 105 and analyzer 114 are mounted on a rotary stage. The rotary stage is controlled, for example by computing system 130, to move to a desired polarization angle, or sequence of polarization angles, and measurement signals are collected at each polarization angle. Alternatively, other polarization control mechanisms may be employed. For example, simultaneous measurement of polarization components by channel separation or polarization control mechanisms (e.g., soleil babinet compensator, waveplates, liquid crystal polarization controller, or other electro-optic polarization controllers) may be implemented.

In some other embodiments, polarizer 105 is a rotating polarizing element. In these embodiments, polarizer 105 is rotated at a constant speed, and the detector signal is acquired at pre-defined frame rate. In these embodiments, system 100 operates as a multiple AOI spectroscopic Ellipsometer (SE).

In another further aspect, a compensator (e.g., compensator 106) is added in the illumination path after the polarizer and another compensator (e.g., compensator 113) is added in the collection path before the analyzer. If the polarizer and collection side compensator are continually rotating during the data acquisition, then the metrology system operates as a multiple AOI rotating polarizer, rotating compensator (RPRC) system. If the polarizer stays at the fixed position and both the illumination side compensator and the illumination side compensator rotate during data acquisition, the system operates as a multiple AOI rotating compensator, rotating compensator (RCRC) system.

Although, as depicted in FIG. 1, system 100 includes polarizer 105, analyzer 107, compensator 106, and compensator 113, in some other embodiments, any or all of these elements may not be employed. Thus, in general, the use of these elements is optional.

As described hereinbefore, a set of illumination apertures (before beam shaping optics, after beam shaping optics, or both) is selected to define the illumination spot size on the specimen. In addition, in some embodiments, the set of illumination apertures is paired with a set of collection apertures to define the range of AOIs detected by the pupil detector. The sets of illumination and collection apertures may be fixed or programmable, and can be based on physical apertures, SLMs, or any other suitable selective mechanism.

Figure 9A:
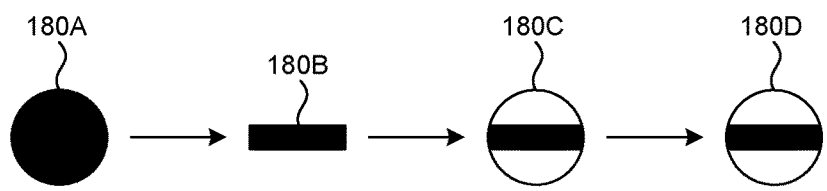
FIGS. 9A-9C depict illumination and collection aperture selections for three exemplary measurement applications, respectively.
Figure 9B:
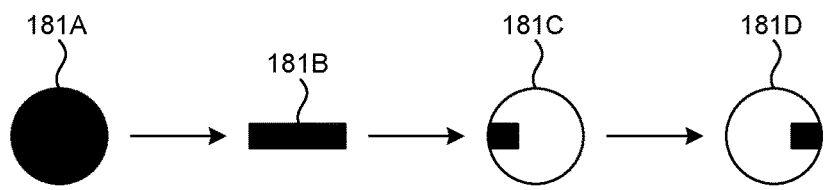
Figure 9C:
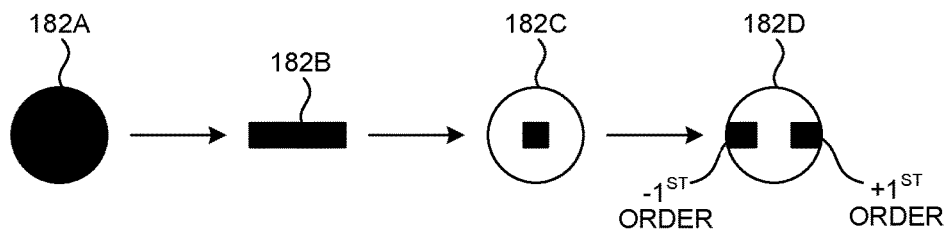

FIGS. 9A-9C depict illumination and collection aperture selections for three exemplary measurement applications.

FIG. 9A depicts several views of the beam intensity profile in a spectroscopic BPR system for zeroth order measurements of CD signals of grating targets having a small pitch (i.e., pitch<136 nanometers) or zeroth order measurements of thin films. In this example, the wavelength ranges from approximately 260 nanometers to approximately 800 nanometers.

FIG. 9A depicts the intensity cross-section 180A of collimated illumination beam 119 before interaction with beam shaping optics 107. FIG. 9A also depicts the intensity cross-section 180B of collimated illumination beam 119 after interaction with beam shaping optics 107. In this example, there is no blocking by either illumination aperture 108 or collection aperture 115. Hence, the intensity cross-section 180C entering objective 111 and the intensity cross-section 180D entering wavelength dispersive element 117 reflect the narrow line beam shape imposed by beams shaping optics 107.

FIG. 9B depicts several views of the beam intensity profile in a spectroscopic BPR system for zeroth order measurements of CD signals of grating targets having a relatively large pitch (i.e., pitch between 136 and 500 nanometers). In this example, the wavelength ranges from approximately 190 nanometers to approximately 800 nanometers.

FIG. 9B depicts the intensity cross-section 181A of collimated illumination beam 119 before interaction with beam shaping optics 107. FIG. 9B also depicts the intensity cross-section 181B of collimated illumination beam 119 after interaction with beam shaping optics 107. In this example, illumination aperture 108 is configured to block AOIs less than 32 degrees. After interaction with illumination aperture 108, the intensity cross-section 181C entering objective 111 reflects this blockage. Similarly, collection aperture 115 is configured to block AOIs less than 32 degrees. After interaction with collection aperture 115, the intensity cross-section 181D entering wavelength dispersive element 111 reflects this blockage. This effectively blocks collected light having a non-zero diffraction order. As a result, detector 118 senses light for AOIs greater than 32 degrees.

FIG. 9C depicts several views of the beam intensity profile in a spectroscopic BPR system for first order measurements of overlay structures having relatively large pitch (a.k.a., scatterometry overlay measurements).

FIG. 9C depicts the intensity cross-section 182A of collimated illumination beam 119 before interaction with beam shaping optics 107. FIG. 9C also depicts the intensity cross-section 182B of collimated illumination beam 119 after interaction with beam shaping optics 107. In this example, illumination aperture 108 is configured to block AOIs greater than 12 degree. After interaction with illumination aperture 108, the intensity cross-section 182C entering objective 111 reflects this blockage. Conversely, collection aperture 115 is configured to block AOIs less than 12 degrees. After interaction with collection aperture 115, the intensity cross-section 182D entering wavelength dispersive element 111 reflects this blockage. The collection aperture effectively blocks collected light having zero diffraction order. As a result, detector 118 senses light with AOIs greater than 12 degrees, which in this example, includes −1st order and +1st order diffracted light.

In another further aspect, a beam shaping optic located in the illumination path is configured to rotate the narrow line beam illumination to a desired azimuth angle. As described hereinbefore, beam shaping optics (e.g., beam shaping optics 107) effectively collapse the azimuth illumination components to a single azimuth value. However, by effectively rotating the narrow line beam illumination about the beam axis, the effective azimuth angle is changed. For some two dimensional measurement targets, such as a CD line-space grating, and some three dimensional measurement targets, such as a complex fin structure, measurement sensitivity is improved when illumination is provided to the target at one or more specific azimuth angles.

In one embodiment, beam shaping optics 107 includes a SLM configured to receive the collimated illumination light 119 and generate a narrow line beam oriented at a programmable illumination azimuth angle with respect to the sample under measurement.

In some embodiments, another SLM is located in the collection path to maintain the orientation of the collection beam with respect to the wavelength dispersive element 117 and detector 118 for any change in beam azimuth angle. Computing system 130 is configured to coordinate changes in state of the illumination SLM and the collection SLM to maintain angular alignment for any change in beam azimuth angle. In some other embodiments, the image projected onto the detector is rotated in software to account for rotations induced by a change in azimuth angle.

In another embodiment, beam shaping optics 107 depicted in FIG. 1 includes a pair of cylindrical mirrors each mounted to a rotary motion stage. Each rotary motion stage is controlled, for example by computing system 130, to change the orientations of the cylindrical mirrors to achieve a desired azimuth angle associated with the narrow line beam. In this manner, system 100 is configured to change the illumination beam azimuth angle with respect to the sample.

In some embodiments, the wavelength dispersive element 117 and detector 118 are also mounted to rotary motion stages to maintain the orientation of the wavelength dispersion and the detector with respect to the collection beam. Computing system 130 is configured to coordinate the motion of the cylindrical mirrors, the wavelength dispersive element 117 and detector 118 to maintain angular alignment for any change in beam azimuth angle. The rotary motion stages can be driven by piezo motors, servo motors, or any other suitable rotary actuation system. In some other embodiments, the image projected onto the detector is rotated in software to account for rotations induced by a change in azimuth angle.

Figure 3:
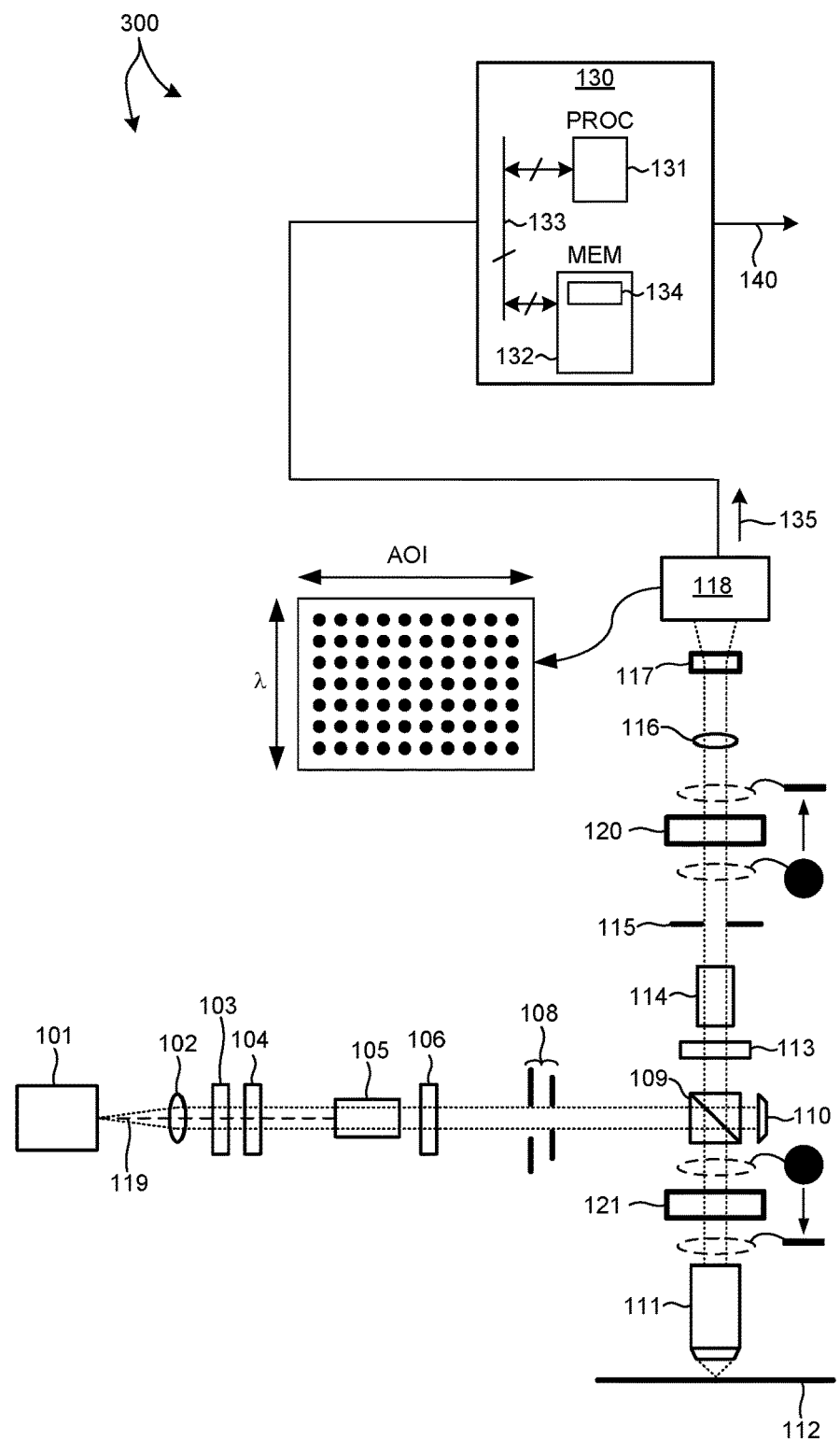
FIG. 3 illustrates another embodiment of a spectroscopic beam profile metrology system 300 for measuring characteristics of a specimen in accordance with the exemplary methods presented herein.

In another embodiment, beam shaping optics 121 depicted in FIG. 3 are located in the common path of a spectroscopic BPR system. Beam shaping optics 121 includes a pair of cylindrical mirrors each mounted to a rotary motion stage. Each rotary motion stage is controlled, for example by computing system 130, to change the orientations of the cylindrical mirrors to achieve a desired azimuth angle associated with the narrow line beam. In this manner, system 300 is configured to change the illumination beam azimuth angle with respect to the sample.

In this embodiment, the beam shape is recovered as a circular beam after passing back through beam shaping optics 121. Additional beam shaping optics 120 located in the collection path reshape the circular beam into a narrow line shape beam before dispersion onto detector 118.

Figure 10A:
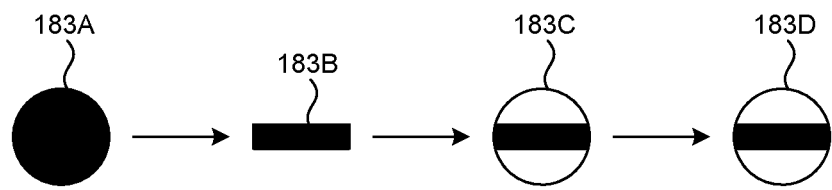
FIGS. 10A-C depict beam intensity profiles associated with three different azimuth angle selections, respectively.
Figure 10B:
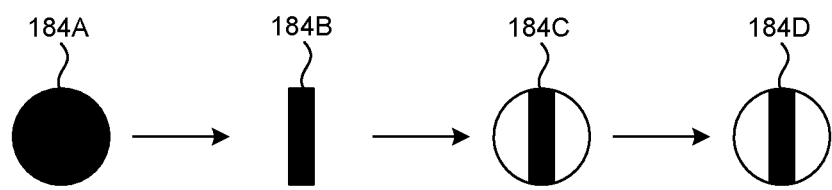
Figure 10C:
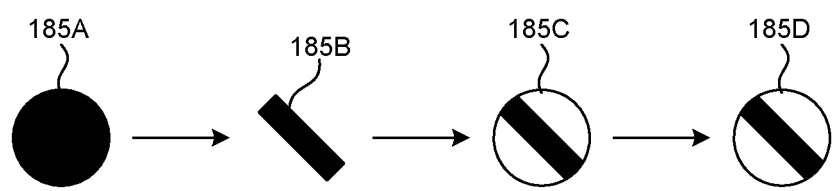

FIGS. 10A-C depict beam intensity profiles associated with three different azimuth angle selections.

FIG. 10A depicts several views of the beam intensity profile in a spectroscopic BPR system for a zero azimuth angle. Intensity cross-section 183A of collimated illumination beam 119 depicts the beam profile intensity of the illumination beam before interaction with beam shaping optics 107. Intensity cross-section 183B depicts the beam profile intensity of the illumination beam after interaction with beam shaping optics 107. For explanatory purposes, the illumination beam azimuth angle depicted in FIG. 10A can be defined as the zero azimuth angle. Intensity cross-section 183C at the entrance of objective 111 and intensity cross-section 183D at the entrance to wavelength dispersive element 117 reflect the zero azimuth angle.

FIG. 10B depicts several views of the beam intensity profile in a spectroscopic BPR system for a ninety degree azimuth angle. Intensity cross-section 184A of collimated illumination beam 119 depicts the beam profile intensity of the illumination beam before interaction with beam shaping optics 107. Intensity cross-section 184B depicts the beam profile intensity of the illumination beam after interaction with beam shaping optics 107. In this example, the configuration of beam shaping optics 107 is changed such that the illumination beam azimuth angle is ninety degrees with respect to the zero azimuth angle described with reference to FIG. 10A. Intensity cross-section 184C at the entrance of objective 111 and intensity cross-section 184D at the entrance to wavelength dispersive element 117 reflect the ninety degree azimuth angle.

FIG. 10C depicts several views of the beam intensity profile in a spectroscopic BPR system for a forty five degree azimuth angle. Intensity cross-section 185A of collimated illumination beam 119 depicts the beam profile intensity of the illumination beam before interaction with beam shaping optics 107. Intensity cross-section 185B depicts the beam profile intensity of the illumination beam after interaction with beam shaping optics 107. In this example, the configuration of beam shaping optics 107 is changed such that the illumination beam azimuth angle is forty five degrees with respect to the zero azimuth angle described with reference to FIG. 10A. Intensity cross-section 185C at the entrance of objective 111 and intensity cross-section 185D at the entrance to wavelength dispersive element 117 reflect the forty five degree azimuth angle.

As described hereinbefore, in some embodiments, a beam shaping optic is located in the illumination path to rotate the narrow line beam illumination to a desired azimuth angle. Also, in some embodiments, as described hereinbefore, a set of illumination apertures is paired with a set of collection apertures to define the range of AOIs detected by the pupil detector. In general, a spectroscopic BPR system such as system 100 may be configured for both azimuth selection and AOI selection.

Figure 11A:
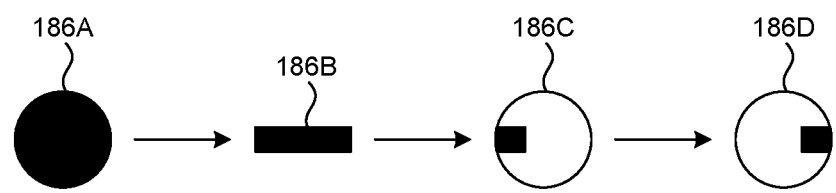
FIGS. 11A-B depict beam intensity profiles associated with two different azimuth angle selections and an AOI selection.
Figure 11B:
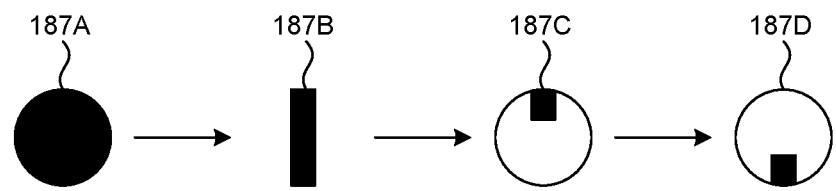

FIGS. 11A-B depict beam intensity profiles associated with two different azimuth angle selections and an AOI selection.

FIG. 11A depicts several views of the beam intensity profile in a spectroscopic BPR system for a zero azimuth angle. Intensity cross-section 186A of collimated illumination beam 119 depicts the beam profile intensity of the illumination beam before interaction with beam shaping optics 107. Intensity cross-section 186B depicts the beam profile intensity of the illumination beam after interaction with beam shaping optics 107. For explanatory purposes, the illumination beam azimuth angle depicted in FIG. 11A is defined as the zero azimuth angle. In this example, illumination aperture 108 is configured to block AOIs less than 32 degrees. After interaction with illumination aperture 108, the intensity cross-section 186C entering objective 111 reflects this blockage. Similarly, collection aperture 115 is configured to block AOIs less than 32 degrees. After interaction with collection aperture 115, the intensity cross-section 186D entering wavelength dispersive element 117 reflects this blockage. This effectively blocks collected light having a non-zero diffraction order. As a result, detector 118 senses light for AOIs greater than 32 degrees at zero azimuth angle.

FIG. 11B depicts several views of the beam intensity profile in a spectroscopic BPR system for a ninety degree azimuth angle. Intensity cross-section 187A of collimated illumination beam 119 depicts the beam profile intensity of the illumination beam before interaction with beam shaping optics 107. Intensity cross-section 187B depicts the beam profile intensity of the illumination beam after interaction with beam shaping optics 107. In this example, the configuration of beam shaping optics 107 is changed such that the illumination beam azimuth angle is ninety degrees with respect to the zero azimuth angle described with reference to FIG. 11A. As described with reference to FIG. 11A, illumination aperture 108 is configured to block AOIs less than 32 degrees. After interaction with illumination aperture 108, the intensity cross-section 187C entering objective 111 reflects this blockage. Similarly, collection aperture 115 is configured to block AOIs less than 32 degrees. After interaction with collection aperture 115, the intensity cross-section 187D entering wavelength dispersive element 117 reflects this blockage. This effectively blocks collected light having a non-zero diffraction order. As a result, detector 118 senses light for AOIs greater than 32 degrees at a ninety degree azimuth angle.

In another further aspect, a spectroscopic BPR system is configured to scan the illumination beam along the AOI direction to enable a mapping of the pupil plane. In a further aspect, this pupil scanning mechanism may also be complemented with a second scanning mechanism that scans the field plane to enable averaging over target noise, a reduction of coherence effects, and improved accuracy.

As depicted in FIG. 1, a scanning mirror 143 is located in the illumination path before the beam shaping optics. The scanning mirror is mounted on a tip/tilt motion stage (e.g., piezoelectric driven stage). The tip/tilt motion stage is configured to steer the illumination in plane across the specimen by changing the range of AOIs. When measuring periodic structures characterized by relatively large pitch features, such as a CD grating or SCOL grating, steering the illumination beam with the scanning mirror is employed to select the optimal AOI range.

Figure 13:
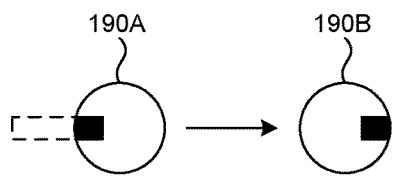
FIG. 13 illustrates a shift in beam intensity profile in a spectroscopic BPR system due to changes in orientation of a scanning mirror 143 located in the illumination path.
Figure 13:
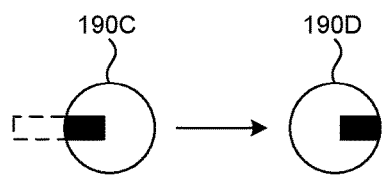

FIG. 13 depicts several views of the shift of beam intensity profile in a spectroscopic BPR system due to changes in orientation of a scanning mirror 143. Intensity cross-section 190A depicts the beam profile intensity of the illumination beam before entrance into objective 111 for a given orientation of the scanning mirror. Intensity cross-section 190B depicts the beam profile intensity of the collection beam entering wavelength dispersive element 117. Intensity cross-section 190C depicts the beam profile intensity of the illumination beam before entrance into objective 111 for a different orientation of the scanning mirror. As illustrated in FIG. 13, this results in a shift of the narrow line beam across the objective 111 in the AOI direction. Intensity cross-section 190D depicts the beam profile intensity of the collection beam entering wavelength dispersive element 117. As illustrated, the shift of the narrow line beam also results in a shift of the collected beam across the wavelength dispersive element 117, and ultimately the detector 118 in the AOI direction. This results in a change in the range of AOIs visible in the objective illumination pupil.

Although, as depicted in FIG. 1, system 100 includes scanning mirror 143, in some other embodiments, a scanning mirror in the illumination path before beam shaping optics 107 may not be employed. Thus, in general, the use of a scanning mirror is optional.

The measurement signals (e.g., measurement signals 135 depicted in FIG. 1) may be used for measurement of critical dimensions (CD), thin film characterization, overlay measurements, focus adjustment, optical system calibration and diagnosis, or any other suitable metrology. Spectroscopic BPR pupil signals 135 contain sample information over a large wavelength and AOI range. Detector signals at each pixel represent the scatterometry signal for a particular AOI and wavelength. Hence, in some embodiments, signals associated with a subset of the pixels are selected for measurement analysis. Different subsets may be selected depending on the measurement application (e.g., CD, TF, overlay, focus/dose, etc.). In addition, different weights may be assigned to different pixel data (i.e., particular wavelengths and AOIs). Signal response metrology (SRM) methods or single parameter isolation (SPI) methods may be employed to select the subset of pixel signals best suited for a particular measurement application. In other embodiments, all of the signals are employed for measurement analysis.

In another further aspect, measurement signals from other measurement modules, such as rotating polarizer spectroscopic ellipsometer (RPSE), rotating analyzer spectroscopic ellipsometer (RASE), rotating compensator spectroscopic ellipsometer (RCSE), rotating polarizer, rotating compensator spectroscopic ellipsometer (RPRC SE), rotating compensator, rotating compensator spectroscopic ellipsometer (RCRC SE), laser driven spectroscopic reflectometer (LDSR), one dimensional beam profile reflectometer (1D-BPR), two dimensional beam profile reflectometer (2D-BPR), etc. may be included in a combined measurement analysis to estimate values of parameters of interest.

In another further aspect, a spectroscopic BPR system includes two wavelength dispersive elements and two corresponding detectors, each configured to detect a different polarization component of the collected light beam.

Figure 2:
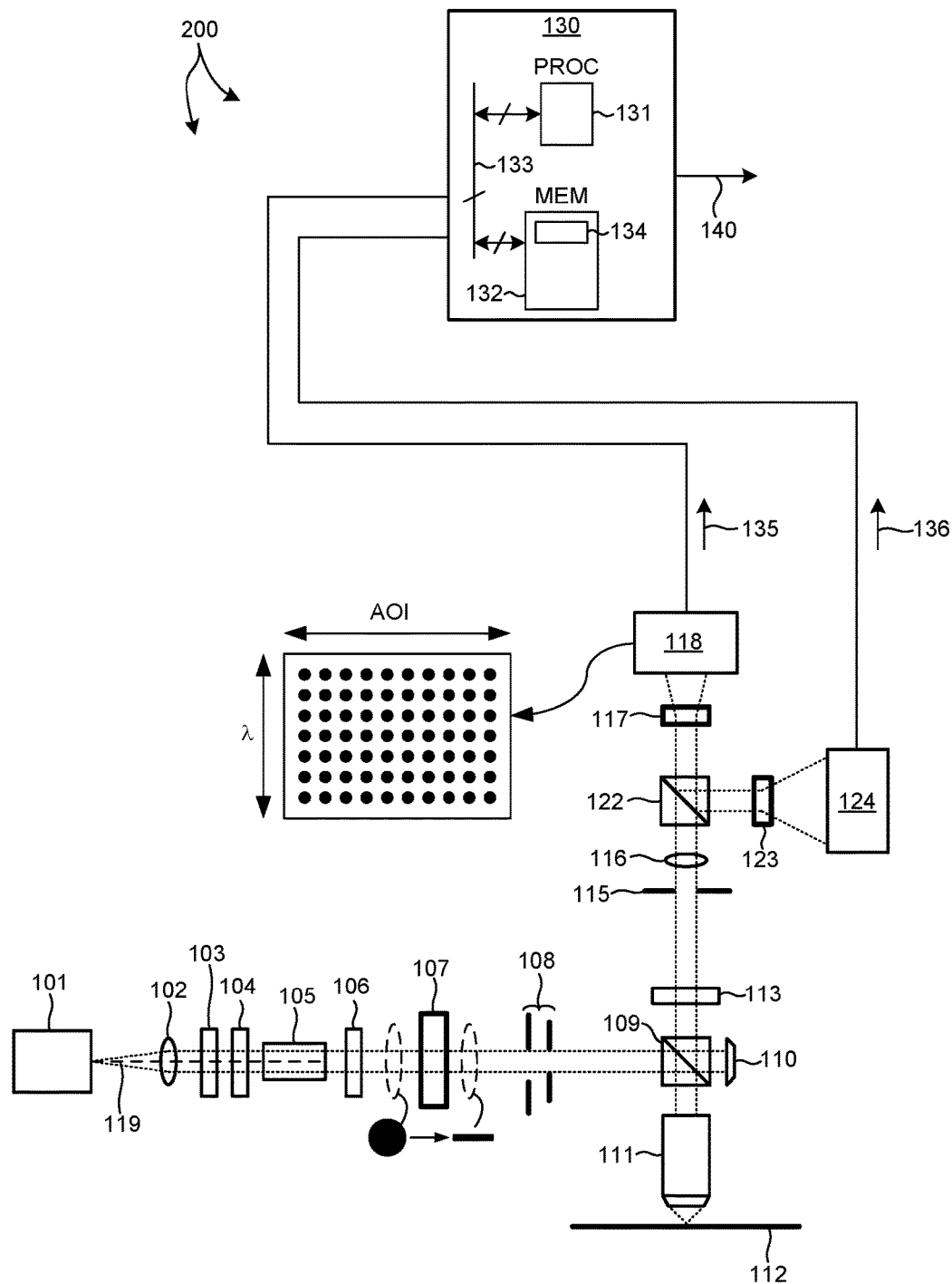
FIG. 2 illustrates another embodiment of a spectroscopic beam profile metrology system 200 for measuring characteristics of a specimen in accordance with the exemplary methods presented herein.

FIG. 2 illustrates a system 200 for measuring characteristics of a specimen in accordance with the exemplary methods presented herein. Like numbered elements are analogous to those described with reference to system 100 depicted in FIG. 1.

As depicted in FIG. 2, system 200 includes polarizing beam splitter 122 in the collection path, rather than an analyzer. Polarizing beam splitter 122 separates the collected light into its p and s polarization components. Each polarization component is directed to a separate wavelength dispersive element and detector (i.e., wavelength dispersive element 117 and detector 118 and wavelength dispersive element 123 and detector 124. In this manner system 200 is configured to simultaneously detect two different polarizations and generate spectroscopic BPR signals 135 and 136 associated with each polarization component, respectively.

In another further aspect, a spectroscopic BPR system includes beam shaping optics in the common path and the collection path. In this manner, the beam shape is a narrow line shape only before entering the objective and any wavelength dispersive elements.

FIG. 3 illustrates a system 300 for measuring characteristics of a specimen in accordance with the exemplary methods presented herein. Like numbered elements are analogous to those described with reference to system 100 depicted in FIG. 1.

As depicted in FIG. 3, beam shaping optics 121 are located in the common path shared by both the illumination path and the collection path. As depicted in FIG. 3, beam shaping optics 121 are configured to reshape the incoming illumination beam to a narrow line shape. After interaction with specimen 112, the collected beam passes through beam shaping optics 121 and beam shaping optics reshapes the collected beam from a narrow line shape to a circular shape.

In addition, beam shaping optics 120 are located in the collection path before wavelength dispersive element 117. Beam shaping optics 120 again reshapes the collected beam from the circular shape to a narrow line shape suitable for dispersion onto detector 118 by wavelength dispersive element 117 as described hereinbefore.

In this embodiment, the beam shape is a narrow line shape only before entering the objective 111 and the wavelength dispersive element 117. Otherwise, the beam shape is circular when passing through other optical components such as the polarizer, analyzer, compensators, illumination apertures, collection apertures, etc.

In another further aspect, a spectroscopic BPR system includes two wavelength dispersive elements and two corresponding detectors. One detector is configured to perform pupil measurements of the specimen under measurement. The other detector is configured to perform field measurements of the same specimen.

Figure 4:
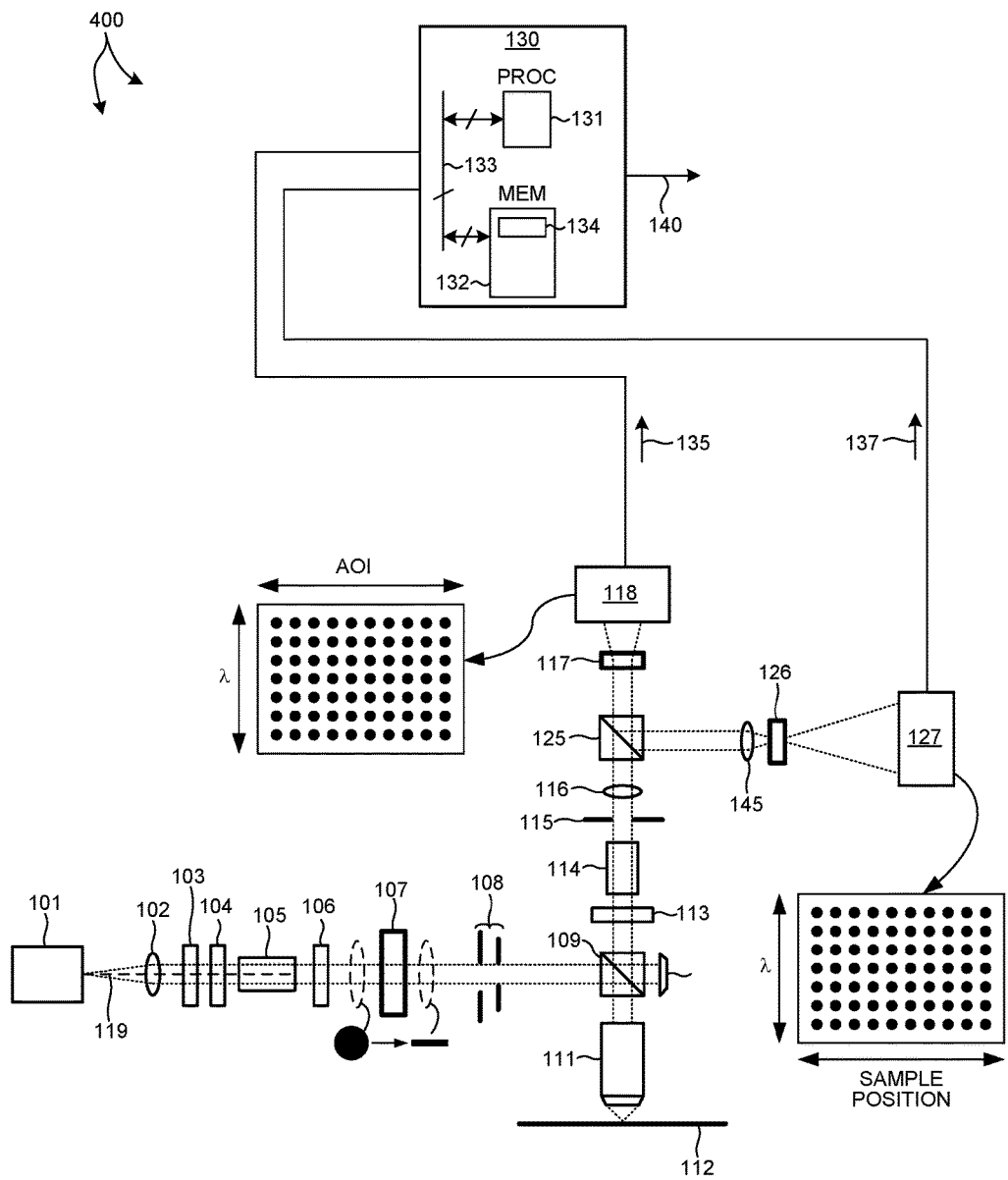
FIG. 4 illustrates another embodiment of a spectroscopic beam profile metrology system 400 for measuring characteristics of a specimen in accordance with the exemplary methods presented herein.

FIG. 4 illustrates a system 400 for measuring characteristics of a specimen in accordance with the exemplary methods presented herein. Like numbered elements are analogous to those described with reference to system 100 depicted in FIG. 1.

As depicted in FIG. 4, system 400 includes a field detector 127 in addition to pupil detector 118. Field detector 127 acquires reflectance signals over a wide wavelength range at multiple samples or sample locations. In the collection path, a beam splitter 125 splits the measurement beam. Beam splitter 125 may include any suitable beam splitting element including, but not limited to, a cubic beam splitter, a metallic coating plate, a dichroic optical coating plate, or other beam splitting mechanism. A portion of the measurement beam is directed toward wavelength dispersive element 117 and pupil detector 118. Another portion of the measurement beam is directed toward wavelength dispersive element 126 and field detector 127. The beam is focused by a focusing optics 145. At the beam focus position, wavelength dispersive element 126 disperses the beam along one dimension of two dimensional detector 127 according to wavelength. The sample position is dispersed along the other dimension of two dimensional detector 127. The signals at each pixel represent the reflectance at a specific sample position and wavelength. These signals 137 are communicated to computing system 130 for measurement analysis. By way of non-limiting example, the detected spectra may be used for measurement of critical dimensions (CD), thin film characterization, overlay measurement, focus adjustment based on zero order signals, optical system calibration and diagnosis, or any other suitable metrology. In some examples, multiple targets are measured simultaneously based on the field measurement signals 137.

In some embodiments, the field collection path includes a set of collection apertures to select signals for projection onto field signal detector 127. In some examples, higher order field signals are selected for projection onto field signal detector 127. The aperture(s) of the selectable field collection aperture may be formed by any suitable device including, but not limited to a mechanical pin-hole, a spatial light modulator (SLM), an apodizer, and any other beam forming and controlling component or sub-system.

In some embodiments, a sliding mirror, or flip-in mirror is employed instead of beam splitter 125. In this embodiments, field and pupil measurements are performed sequentially by selectively removing the sliding mirror in and out of the collection beam path, for example under the control of computing system 130.

In some embodiments, beam splitter 125 diverts a portion of the collected beam to focusing optics 145 for imaging directly onto a two dimensional imaging detector. In these embodiments, the resulting wafer field images can be used for measurement purposes, pattern recognition, image based focusing, or any combination thereof.

In a further aspect, the combined data from pupil detector 118 and field detector 127 is employed to estimate values of parameters of interest, or perform diagnostic tests. In some embodiments, both field and pupil measurement signals are simultaneously detected and processed to estimate one or more structural or process parameter values and to characterize the quality of the measurement. In some embodiments, field measurement signals are processed to estimate one or more structural or process parameter values, and pupil measurement signals are processed to characterize the field measurement conditions. In some other embodiments, pupil measurement signals are processed to estimate one or more structural or process parameter values, and field measurement signals are processed to characterize the pupil measurement conditions.

Field measurement signals are detected at or near the field plane of the measurement system. The field plane of the measurement system is conjugate to the surface of the specimen under measurement. Pupil plane measurement signals are detected at or near the pupil plane of the measurement system. The pupil plane is the Fourier transform of the field plane and is conjugate to the limiting aperture of the objective. In general, light reflected, diffracted, or scattered from different locations on the surface of a specimen under measurement is detected in different locations in the field plane of the measurement system, regardless of the collection angle. In contrast, light reflected, diffracted, or scattered at different angles from the surface of a specimen under measurement is detected in different locations in the pupil plane of the measurement system, regardless of the location of the light interaction on the surface of the specimen.

In some embodiments, both field and pupil measurement signals are simultaneously detected. The detected signals are iteratively processed to estimate one or more structural or process parameter values. More specifically, the value of the at least one structural or process parameter associated with the at least one measurement target is determined based on an iterative regression of the pupil measurement signals with a pupil measurement model and regression of the field measurement signals with a field measurement model.

In one embodiment, computing system 130 determines an estimate of a CD parameter based on spectroscopic BPR signals 135 and determines an estimate of a film stack parameter (e.g., film thickness) based on field signals 137 in an iterative regression analysis.

In this example, a CD measurement model includes a parameterization of the metrology target in terms of the CD parameter of interest. In addition, the CD measurement model includes a parameterization of the measurement tool itself (e.g., wavelengths, angles of incidence, polarization angles, etc.). Similarly, the film stack measurement model includes a parameterization of the metrology target in terms of the film stack parameter of interest (e.g., film thickness). In addition, the film stack measurement model includes a parameterization of the measurement tool itself. In addition, simulation approximations (e.g., slabbing, Rigorous Coupled Wave Analysis (RCWA), etc.) are carefully performed to avoid introducing excessively large errors. Discretization and RCWA parameters are defined.

Machine parameters ($P_{machine}$) are parameters used to characterize the metrology tool itself. Exemplary machine parameters include angle of incidence (AOI), analyzer angle (A0), polarizer angle (P0), illumination wavelength, numerical aperture (NA), etc. Specimen parameters ($P_{specimen}$) are parameters used to characterize the geometric and material properties of the specimen. For a thin film specimen, exemplary specimen parameters include refractive index, dielectric function tensor, nominal layer thickness of all layers, layer sequence, etc.

For measurement purposes, the machine parameters of the multi-target model are treated as known, fixed parameters and the specimen parameters of the measurement model, or a subset of specimen parameters, are treated as unknown, floating parameters. The floating parameters are resolved by a fitting process (e.g., regression, library matching, etc.) that produces the best fit between theoretical predictions and measured data. The unknown specimen parameters, $P_{specimen}$, are varied and the model output values are calculated until a set of specimen parameter values are determined that results in a close match between the model output values and the measured values.

In an iterative regression analysis, computing system 130 fits measured pupil signals to the CD measurement model to arrive at an estimated CD parameter value. The film stack parameters present in the CD measurement model are floated during this regression. Then computing system 130 fits the measured field signals to the film stack model to arrive at an estimated film stack parameter value (e.g., film thickness). The CD parameter values present in the film stack model are fixed to the values determined by the previous regression of pupil signals to the CD measurement model. Subsequently, computing system 130 again fits the measured pupil signals to the CD measurement model to arrive at an updated estimate of the CD parameter value. At this iteration, the film stack parameters present in the CD measurement model are fixed to the values determined by the previous regression of the field signals to the film stack model. This iteration continues until the parameter estimates reach sufficient accuracy.

In another further aspect, both field and pupil measurement signals are simultaneously detected. The detected signals are processed in a combined analysis to estimate one or more structural or process parameter values. In these examples, the measurement model is a combined measurement model that links structural parameters, material parameters, or a combination of structural and material parameters of the metrology target(s) for both pupil and field measurements.

In another further aspect, a spectroscopic BPR system includes a beam combining element 128 in the measurement path before the objective. An auto-focus probe beam, a pattern recognition probe beam, or a combination of both, are combined with the illumination beam before entering the objective. Similarly, an auto-focus signal beam, a pattern recognition signal beam, or a combination of both, are extracted from the collection beam after exiting the objective. The beam combining element 128 is fixed in location with respect to the measurement path, thus increasing reliability and accuracy. Since both the measurement beam and the auto-focus beam probe the sample simultaneously, system 500 is able to acquire measurement data while the auto-focus system is continuously engaging in focus measurement. This improves the signal quality and reduces focus time.

Figure 5:
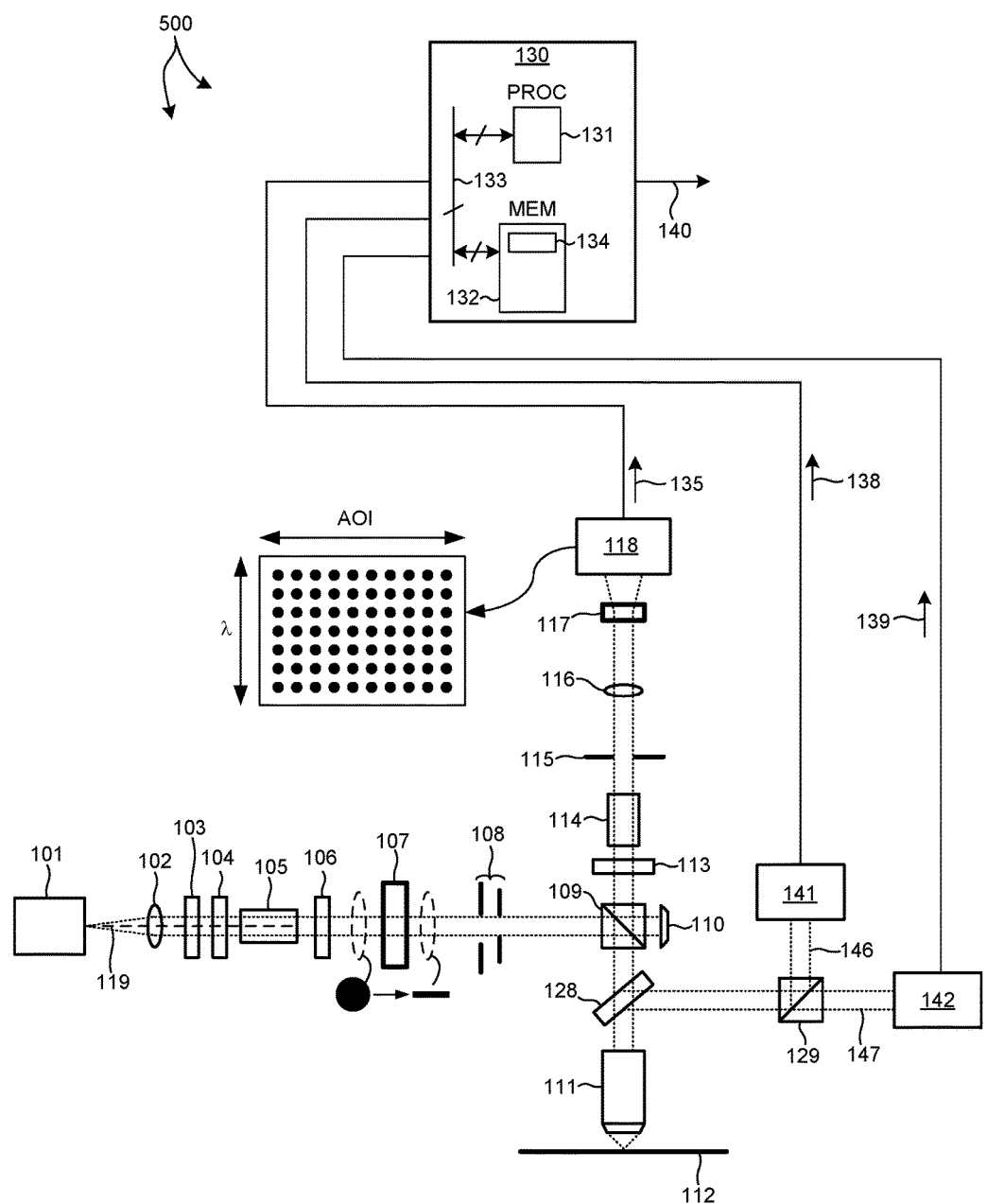
FIG. 5 illustrates another embodiment of a spectroscopic beam profile metrology system 500 for measuring characteristics of a specimen in accordance with the exemplary methods presented herein.

FIG. 5 illustrates a system 500 for measuring characteristics of a specimen in accordance with the exemplary methods presented herein. Like numbered elements are analogous to those described with reference to system 100 depicted in FIG. 1.

As described herein, the illumination and collection beams in front of the objective are narrow line shaped beams. This allows an auto-focus probe beam 146, a pattern-recognition probe beam 147, or both, to be combined with the measurement beams before entering the high NA objective.

An auto focus subsystem 141 generates an auto-focus probe beam 146 that is directed through beam splitter 129 and optical combining element 128 to objective 111. Light collected by objective 111 in response to auto-focus probe beam 146 is returned to auto focus subsystem 141 through the same path. Based on the received signals, auto focus subsystem 141 generates auto-focus signals 138 which are communicated to computing system 130. In one example, computing system 130 causes the focal position of specimen 112 to be changed based on auto-focus signals 138.

Similarly, a pattern recognition subsystem 142 generates a pattern recognition probe beam 147 that is directed through beam splitter 129 and optical combining element 128 to objective 111. Light collected by objective 111 in response to pattern recognition probe beam 147 is returned to auto focus subsystem 142 through the same path. Based on the received signals, pattern recognition subsystem 142 generates pattern recognition signals 139 (e.g., images) which are communicated to computing system 130. In one example, computing system 130 causes the position of specimen 112 based on the pattern recognition signals 139. In this manner, the pattern recognition signals 139 are used to navigate over the surface of specimen 112.

As depicted in FIG. 5, system 500 includes an optical combining element 128 in the common path in front of objective 111.

Figure 7A:
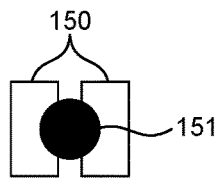
FIGS. 7A-7C depict a half fold mirror 150 employed as a beam combining element in the spectroscopic beam profile metrology systems described herein.
Figure 7B:
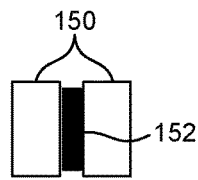
Figure 7C:
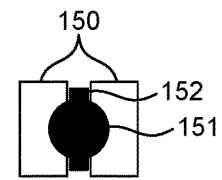

In some embodiments, optical combining element 128 is a narrow fold mirror having a narrow line shaped air gap. The narrow fold mirror can be made by coplanar alignment of two or four individual mirror cells. Alternatively, one or two slots are cut on a single glass substrate before coating with a reflective layer. FIGS. 7A-7C depict a half fold mirror 150 as the optical combining element 128. FIG. 7A depicts a beam profile 151 having a circular profile. Such a profile is representative of an auto-focus beam, a pattern recognition beam, or both. As depicted in FIG. 7A, a significant portion of beam profile 151 is reflected by half fold mirror 150. FIG. 7B depicts a narrow line beam profile 152 that is representative of an illumination beam profile, collection beam profile, or both. As depicted in FIG. 7B, all of the narrow beam profile 152 passes through the air gap in the half fold mirror 150. FIG. 7C depicts the combination of the narrow line beam profile 152 and the circular beam profile 151 interacting with half fold mirror 150.

Figure 7D:
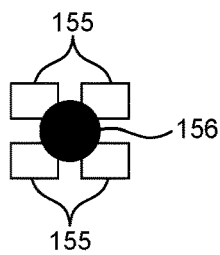
FIGS. 7D-7F depict a four-cell fold mirror 155 employed as a beam combining element in the spectroscopic beam profile metrology systems described herein.
Figure 7E:
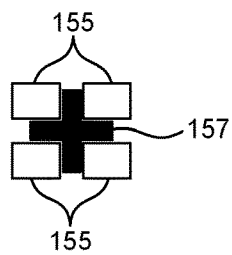
Figure 7F:
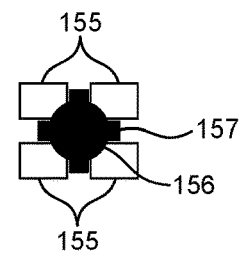

FIGS. 7D-7F depict a four-cell fold mirror 155 as the optical combining element 128. FIG. 7D depicts a beam profile 156 having a circular profile. As depicted in FIG. 7D, a significant portion of beam profile 156 is reflected by four-cell mirror 155. FIG. 7E depicts a narrow line beam profile 157 that is representative of an illumination beam profile, collection beam profile, or both. As depicted in FIG. 7E, all of the narrow beam profile 157 passes through the air gap in four-cell fold mirror 155. FIG. 7F depicts the combination of the narrow line beam profile 157 and the circular beam profile 156 interacting with four-cell fold mirror 155.

Figure 8A:
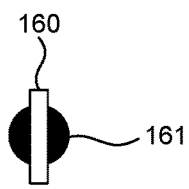
FIGS. 8A-8C depict a narrow line shaped mirror 160 employed as a beam combining element in the spectroscopic beam profile metrology systems described herein.
Figure 8B:
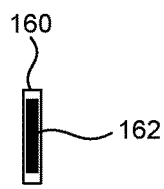
Figure 8C:
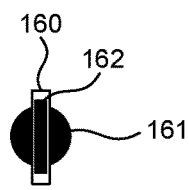

In some other embodiments, optical element 128 is a flat narrow mirror. FIGS. 8A-8C depict a narrow line shaped mirror 160 as the optical combining element 128. FIG. 8A depicts a beam profile 161 having a circular profile. Such a profile is representative of an auto-focus beam, a pattern recognition beam, or both. As depicted in FIG. 8A, a significant portion of beam profile 161 passes through narrow, line shaped mirror 160. FIG. 8B depicts a narrow line beam profile 162 that is representative of an illumination beam profile, collection beam profile, or both. As depicted in FIG. 8B, all of the narrow beam profile 162 is reflected by narrow, line shaped mirror 160. FIG. 8C depicts the combination of the narrow line beam profile 162 and the circular beam profile 161 interacting with narrow, line shaped mirror 160.

Figure 8D:
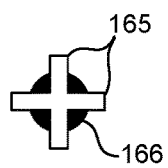
FIGS. 8D-8F depict a narrow cross shaped mirror 165 as a beam combining element in the spectroscopic beam profile metrology systems described herein.
Figure 8E:
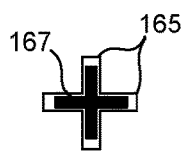
Figure 8F:
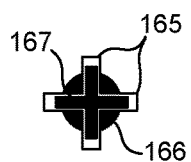

FIGS. 8D-8F depict a narrow cross shaped mirror 165 as the optical combining element 128. FIG. 8D depicts a beam profile 166 having a circular profile. Such a profile is representative of an auto-focus beam, a pattern recognition beam, or both. As depicted in FIG. 8D, a significant portion of beam profile 166 passes through narrow, cross shaped mirror 165. FIG. 8E depicts a narrow line beam profile 167 that is representative of an illumination beam profile, collection beam profile, or both. As depicted in FIG. 8E, all of the narrow beam profile 167 is reflected by narrow, cross shaped mirror 165. FIG. 8F depicts the combination of the narrow line beam profile 167 and the circular beam profile 166 interacting with narrow, cross shaped mirror 165.

As depicted in FIG. 5, system 500 includes an optical combining element 128 in the common path in front of objective 111 such that the measurement beam passes through optical combining element 128. Such a configuration is suitable for the narrow fold mirror designs described with reference to FIGS. 7A-7F. The narrow mirror designs described with reference to FIGS. 8A-8F may also be implemented as part of system 500 if objective 111 were reoriented such that the auto-focus and pattern recognition beams pass directly through beam combining element 128 and the measurement beams are turned by beam combining element 128.

In another aspect, a hyperspectral detector is employed to detect the spectral component of a spectroscopic beam profile metrology system.

Figure 6:
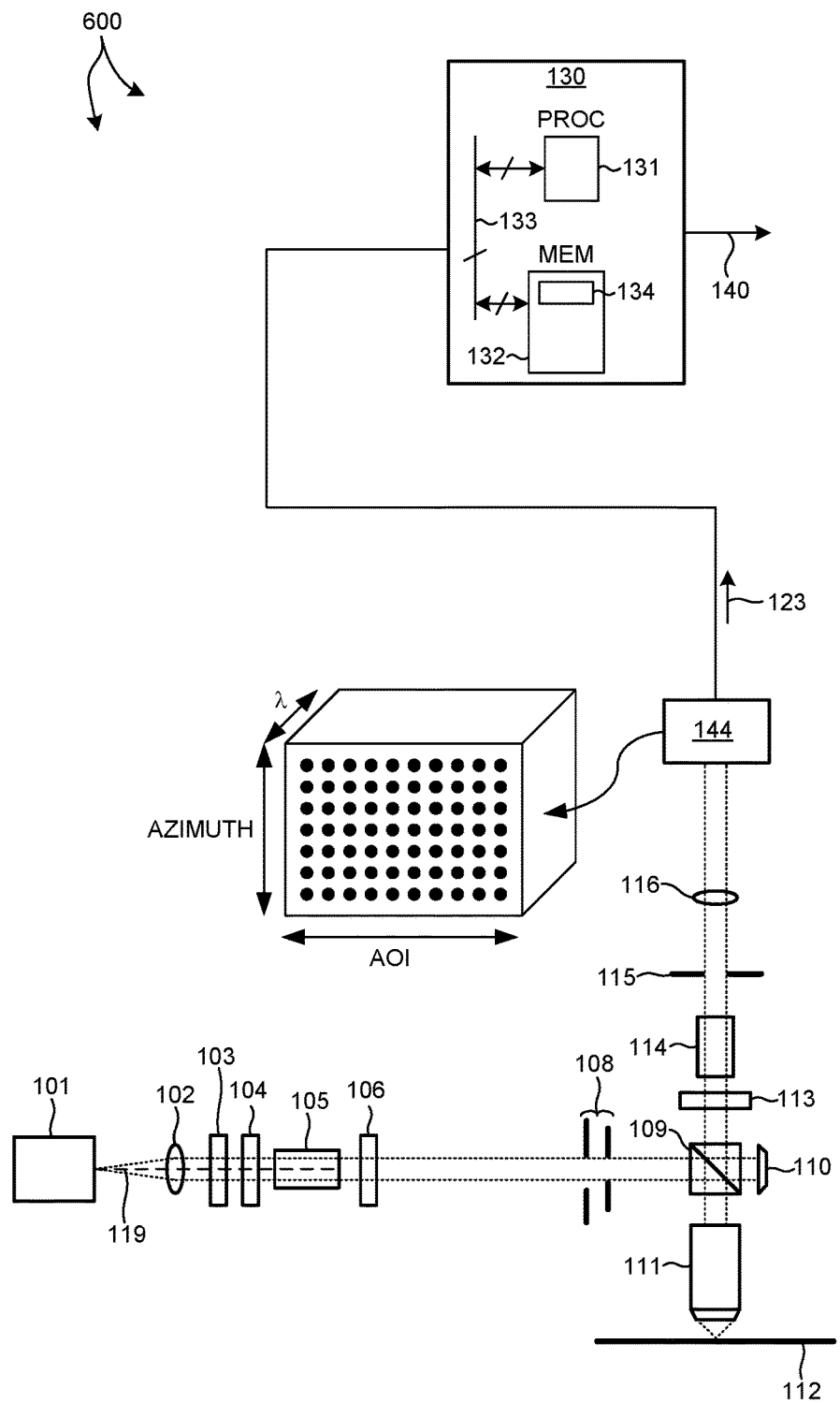
FIG. 6 illustrates another embodiment of a spectroscopic beam profile metrology system 600 for measuring characteristics of a specimen in accordance with the exemplary methods presented herein.

FIG. 6 illustrates a system 600 for measuring characteristics of a specimen in accordance with the exemplary methods presented herein. Like numbered elements are analogous to those described with reference to system 100 depicted in FIG. 1.

System 600 includes a hyperspectral detector 144 as the pupil detector. Detector 144 is configured to measure wavelength components by penetration depth (vertical detector), index of refraction, or another wavelength dependent property of the detector. In some embodiments, a CMOS hyperspectral detector 144 measures azimuth and AOI in two dimensions (e.g., across the face of the detector) and resolves wavelength information in a third dimension orthogonal to the two planar dimensions (e.g., depth into the detector). In some other embodiments, each "pixel" on the face of the hyperspectral detector is a spectrometer including a small grating structure that spreads the incoming light onto a number of different light sensitive elements. In general, a hyperspectral detector can be used as an alternative to the use of a wavelength dispersive element and detector as described with reference to FIGS. 1-5, or a hyperspectral detector can be used to complement these systems.

Figure 14:
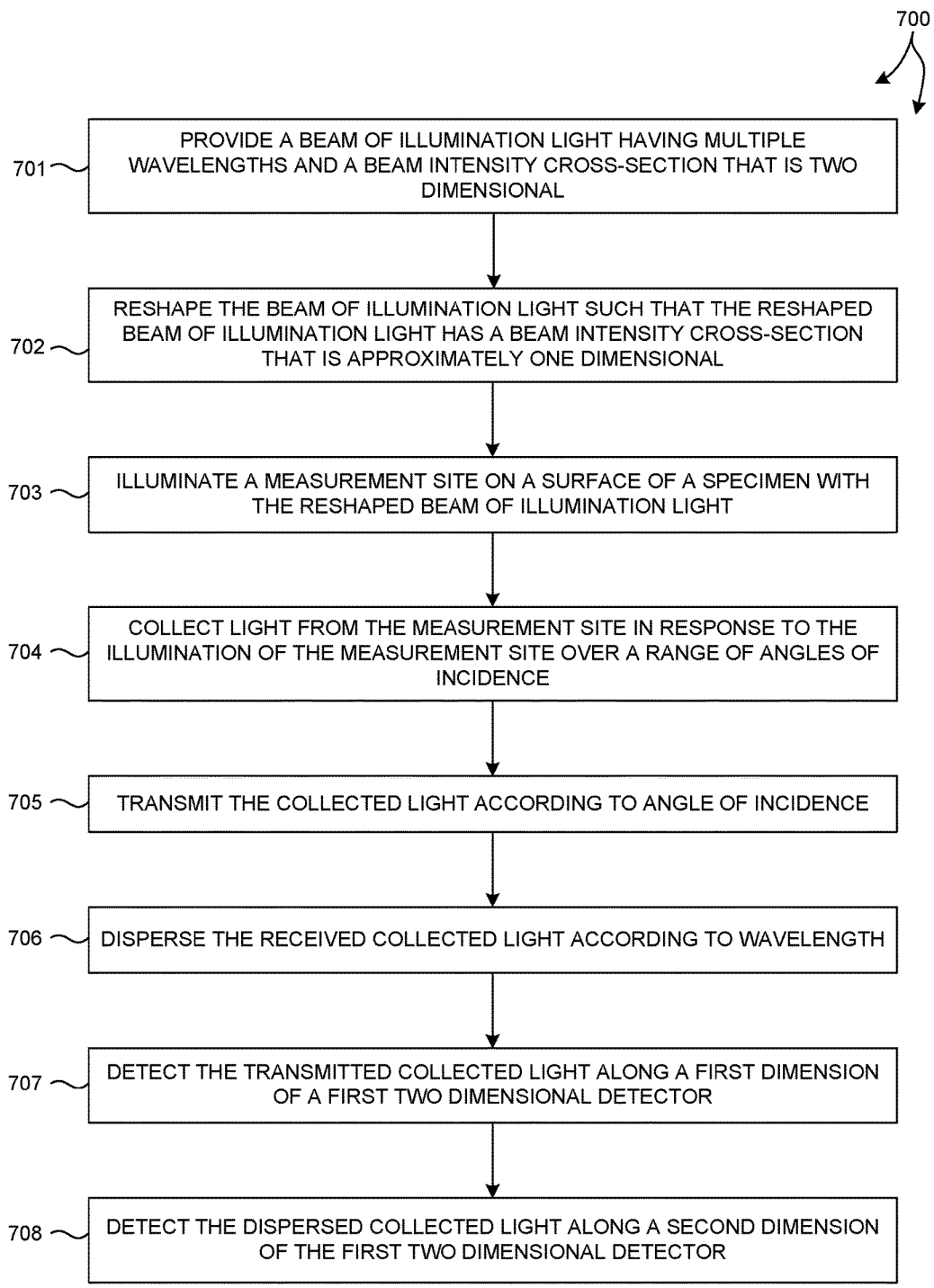
FIG. 14 is a flowchart illustrative of a method 700 suitable for implementation by a metrology system such as metrology system 100 illustrated in FIG. 1 of the present invention.

FIG. 14 illustrates a method 700 suitable for implementation by a metrology system such as metrology systems 100, 200, 300, 400, and 500 illustrated in FIGS. 1-5, respectively. In one aspect, it is recognized that data processing blocks of method 700 may be carried out via a pre-programmed algorithm executed by one or more processors of computing system 130, or any other general purpose computing system. It is recognized herein that the particular structural aspects of any of the aforementioned metrology systems do not represent limitations and should be interpreted as illustrative only.

In block 701, a beam of illumination light having multiple wavelengths is provided, for example, by illumination source 101. The beam intensity cross-section is two dimensional.

In block 702, the beam of illumination light is reshaped, for example, by beam shaping element 107, such that the reshaped beam of illumination light has a beam intensity cross-section that is approximately one dimensional.

In block 703, a measurement site on a surface of a specimen is illuminated with the reshaped beam of illumination light.

In block 704, light from the measurement site is collected, for example, by objective 111, in response to the illumination of the measurement site over a range of angles of incidence.

In block 705, the collected light is transmitted according to angle of incidence, for example, by wavelength dispersive element 117.

In block 706, the collected light is dispersed according to wavelength, for example, by wavelength dispersive element 117.

In block 707, the transmitted collected light is detected along a first dimension of a first two dimensional detector, such as detector 118.

In block 708, the dispersed collected light is detected along a second dimension of the first two dimensional detector, such as detector 118.

It should be recognized that the various steps described throughout the present disclosure may be carried out by a single computer system 130 or, alternatively, a multiple computer system 130. Moreover, different subsystems of the spectroscopic beam profile metrology systems described herein may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the detectors of the spectroscopic beam profile metrology systems described herein in any manner known in the art. For example, the one or more computing systems 130 may be coupled to computing systems associated with the detectors of system 100. In another example, the detectors may be controlled directly by a single computer system coupled to computer system 130.

The computer system 130 of the metrology system 100 may be configured to receive and/or acquire data or information from the subsystems of the system (e.g., detector 118, and the like) by a transmission medium that may include wireline and/or wireless portions. In this manner, the transmission medium may serve as a data link between the computer system 130 and other subsystems of the system 100.

Computer system 130 of system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or other external systems). For example, the computing system 130 may be configured to receive measurement data from a storage medium (i.e., memory 132 or an external memory) via a data link. For instance, spectral measurement results obtained using detector 118 may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a parameter value 140 determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

Typical semiconductor metrology, such as spectroscopic ellipsometry, involves the collection and analysis of zero order diffracted light. However, in another aspect, diffracted light having a diffraction order different from zero is collected and analyzed to determine the value of at least one structural parameter that is indicative of a geometric error induced by a multiple patterning process. In some embodiments, a single diffraction order different from zero (e.g., -1 or 1) is collected and analyzed to determine the value of at least one structural parameter that is indicative of a geometric error induced by a single or multiple patterning process.

The relation between the angle of incidence and the 0th order angle is given by equation (1), where $\theta_{AOI}$ is the angle of incidence of the illumination light and $\theta_{AOI}$ is the angle of the 0th order.

$$\theta_{AOI} = \theta_{0th} \tag{1}$$

The numerical aperture of the $-1^{st}$ order is related to the numerical aperture of the $0^{th}$ order, the wavelength of the illumination light, $\lambda$, and the pitch of the grating structure, P, as given by equation (2).

$$NA_{-1st} = NA_{0th} - \frac{\lambda}{P} \tag{2}$$

In some other embodiments, solid immersion techniques may be employed to include light diffracted at higher order (i.e., any order different from zero) within the pupil of the system. In this manner, the same detector may be employed to detect both zero order diffracted light and higher order diffracted light, even for systems without a large collection NA.

In yet another further aspect, short wavelength components of the illumination beam are employed to highlight whether a structure is periodic based on the response of the structure to short wavelength illumination. Sufficiently short illumination wavelengths enable the capture of first order diffraction elements that would otherwise be evanescent. In general, it is desireable to reduce the wavelengths associated with the illumination light as much as possible to enhance measurement sensitivity for small pitch structure. Hence, in some embodiments, vacuum ultraviolet illumination light may be desireable.

In some embodiments, it may be desireable to employ apertures to separate collected light according to diffraction order, i.e. separate "0" and "−1" order in collection. If illumination and collection modes are such that "0" and "−1" orders overlap and interfere, it may be desireable to implement beam scanning over the grating to evaluate fringe visibility and determine the strength of the 1st order.

In general, detection of higher order diffracted light does not have to be in the pupil plane; wafer plane measurements could also be implemented.

In a further aspect, measurement data from multiple targets is collected for measurements. In some examples, the use of measurement data associated with multiple targets eliminates, or significantly reduces, the effect of under layers in the measurement result. In one example, measurement signals from two targets are subtracted to eliminate, or significantly reduce, the effect of under layers in each measurement result. The use of measurement data associated with multiple targets increases the sample and process information embedded in the model.

In another further aspect, measurement data from both measurement targets and assist targets that may be found on-device or within scribe lines is collected for measurements.

In some examples, the measurement methods described herein are implemented as an element of a SpectraShape® optical critical-dimension metrology system available from KLA-Tencor Corporation, Milpitas, Calif., USA.

In some other examples, the measurement methods described herein are implemented off-line, for example, by a computing system implementing AcuShape® software available from KLA-Tencor Corporation, Milpitas, Calif., USA.

In another example, the methods and systems described herein may be applied to overlay metrology. Grating measurements are particularly relevant to the measurement of overlay. The objective of overlay metrology is to determine shifts between different lithographic exposure steps. Performing overlay metrology on-device is difficult due to the small size of on-device structures, and the typically small overlay value.

For example, the pitch of typical scribe line overlay metrology structures varies from 200 nanometers to 2,000 nanometers. But, the pitch of on-device, overlay metrology structures is typically 100 nanometers or less. In addition, in a nominal production environment, the device overlay is only a small fraction of the periodicity of the device structure. In contrast, proxy metrology structures used in scatterometry overlay are frequently offset at larger values, e.g., quarter of the pitch, to enhance signal sensitivity to overlay.

Under these conditions, overlay metrology is performed with sensor architectures having sufficient sensitivity to small offset, small pitch overlay. The methods and systems described herein may be employed to obtain a measurement signal sensitive to overlay based on on-device structures, proxy structures, or both.

In general, the methods and systems for performing semiconductor metrology presented herein may be applied directly to actual device structures or to dedicated metrology targets (e.g., proxy structures) located in-die or within scribe lines.

In yet another aspect, the measurement results described herein can be used to provide active feedback to a process tool (e.g., lithography tool, etch tool, deposition tool, etc.). For example, values of the structural or process parameters determined using the methods described herein can be communicated to a lithography tool to adjust the lithography system to achieve a desired output (e.g., focus and dosage). In a similar way etch parameters (e.g., etch time, diffusivity, etc.) or deposition parameters (e.g., time, concentration, etc.) may be included in a measurement model to provide active feedback to etch tools or deposition tools, respectively.

As described herein, the term "wavelength dispersive element" includes any dispersive element that separates incoming light according to wavelength in any manner, whether linear or non-linear. Under this definition, commonly termed "energy dispersive" elements are included as wavelength dispersive elements for purposes of this patent document.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
a multiple wavelength illumination source configured to provide a beam of illumination light having multiple wavelengths and a beam intensity cross-section that is two dimensional;
a high numerical aperture (NA) objective configured to receive the beam of illumination light, illuminate a measurement site on a surface of a specimen with the beam of illumination light, and collect light from the measurement site in response to the illumination of the measurement site over a range of angles of incidence; and
a hyperspectral detector configured to detect the collected light according to angle of incidence along a first dimension of the hyperspectral detector, detect the collected light according to azimuth angle along a second dimension of the hyperspectral detector, and detect the collected light according to wavelength along a third dimension of the hyperspectral detector.

2. The metrology system of claim 1, wherein a light sensitive surface of the hyperspectral detector is located in a pupil plane of the metrology system.

3. The metrology system of claim 1, wherein the detection of the collected light according to wavelength is based on any of a penetration depth into the hyperspectral detector and an index of refraction of the hyperspectral detector.

4. The metrology system of claim 1, wherein the hyperspectral detector is a three dimensional complementary metal oxide semiconductor (CMOS) sensor.

5. The metrology system of claim 1, wherein the first and second dimensions are aligned with a light sensitive surface of the hyperspectral detector and the third dimension is orthogonal to the first and second dimensions.

6. The metrology system of claim 1, wherein the hyperspectral detector includes a plurality of spectrometers disposed on a surface of the hyperspectral detector, wherein each spectrometer includes a grating structure that disperses incident light onto a plurality of light sensitive elements.

7. The metrology system of claim 1, wherein the hyperspectral detector is further configured to generate a plurality of measurement signals indicative of the collected light detected by the hyperspectral detector, wherein each of the plurality of measurement signals is associated with a measurement of the measurement site at a unique wavelength, angle of incidence, and azimuth angle.

8. The metrology system of claim 7, further comprising:
a computing system configured to:
receive the plurality of measurement signals indicative of the detected light;
determine a value of at least one structural or process parameter associated with the at least one measurement target located at the measurement site based on the measurement signals; and
store the value of the at least one structural or process parameter in a memory.

9. The metrology system of claim 8, wherein the at least one structural or process parameter associated with the at least one measurement target includes any of a critical dimension, a thin film dimension, an overlay measurement, a lithography focus, and a lithography dosage.

10. The metrology system of claim 8, further comprising:
a two dimensional detector configured to detect light collected from the measurement site at or near a field plane of the metrology system and generate one or more field measurement signals indicative of the light detected at or near the field plane; and a computing system configured to:
receive the field measurement signals;
determine a value of at least one structural or process parameter associated with the at least one measurement target based on the measurement signals and the field measurement signals; and
store the value of the at least one structural or process parameter in a memory.

11. The metrology system of claim 10, wherein the determining of the value of the at least one structural or process parameter associated with the at least one measurement target is based on an iterative regression of the plurality of measurement signals with a pupil measurement model and regression of the field measurement signals with a field measurement model.

12. The metrology system of claim 1, wherein the detected light is diffracted from the illuminated measurement site at a diffraction order different from a zero diffraction order.

13. The metrology system of claim 1, further comprising:
a polarizer element located in a path of the beam of illumination light.

14. The metrology system of claim 13, further comprising:
an analyzer element located in a path of the collected light; and
at least one compensator element located in the path of the beam of illumination light, the path of the collected light, or both.

15. The metrology system of claim 14, wherein any of the polarizer element, the analyzer element, and the one or more compensator elements are continuously rotating.

16. The metrology system of claim 1, further comprising:
a beam combining element located in an optical path in front of the high NA objective, wherein the beam combining element is configured to combine an autofocus beam, a pattern recognition beam, or both, with the beam of illumination light received by the objective.

17. A metrology system comprising:
a multiple wavelength illumination source configured to provide a beam of illumination light having multiple wavelengths and a beam intensity cross-section that is two dimensional;
a high numerical aperture (NA) objective configured to receive the beam of illumination light, illuminate a measurement site on a surface of a specimen with the beam of illumination light, and collect light from the measurement site in response to the illumination of the measurement site over a range of angles of incidence and azimuth angles; and
a hyperspectral detector configured to simultaneously detect the collected light according to angle of incidence, azimuth angle, and wavelength.

18. The metrology system of claim 17, wherein the hyperspectral detector is configured to detect the collected light according to angle of incidence along a first dimension of the hyperspectral detector, detect the collected light according to azimuth angle along a second dimension of the hyperspectral detector, and detect the collected light according to wavelength along a third dimension of the hyperspectral detector.

19. The metrology system of claim 17, wherein the hyperspectral detector includes a plurality of spectrometers disposed on a surface of the hyperspectral detector, wherein each spectrometer includes a grating structure that disperses incident light onto a plurality of light sensitive elements, and wherein the collected light incident on each of the spectrometers is associated with a unique combination of angle of incidence and azimuth angle.

20. A method comprising:
providing a beam of illumination light having multiple wavelengths and a beam intensity cross-section that is two dimensional;
illuminating a measurement site on a surface of a specimen with the beam of illumination light;
collecting light from the measurement site in response to the illumination of the measurement site over a range of angles of incidence and a range of azimuth angles;
dispersing the collected light according to wavelength;
simultaneously detecting the collected light according to angle of incidence, azimuth angle, and wavelength across different light sensitive elements of a hyperspectral detector.

* * * * *